US012672918B2

(12) United States Patent
Otto et al.

(10) Patent No.: US 12,672,918 B2
(45) Date of Patent: Jul. 7, 2026

(54) DYNAMIC GAP CAPTURE AND FLEXION WIDGET

(71) Applicant: MAKO Surgical Corp., Weston, FL (US)

(72) Inventors: Jason Otto, Sioux Falls, SD (US);
Kelly Dunn, Fort Lauderdale, FL (US);
Kevin Bechtold, Weston, FL (US);
Emerson Tucker, Weston, FL (US)

(73) Assignee: MAKO SURGICAL CORP., Weston, FL (US)

( * ) Notice: Subject to any disclaimer, the term of this patent is extended or adjusted under 35 U.S.C. 154(b) by 1287 days.

(21) Appl. No.: 17/514,640

(22) Filed: Oct. 29, 2021

(65) Prior Publication Data

US 2022/0183767 A1 Jun. 16, 2022

Related U.S. Application Data

(60) Provisional application No. 63/226,858, filed on Jul. 29, 2021, provisional application No. 63/177,034,
(Continued)

(51) Int. Cl.
*A61B 34/00* (2016.01)
*A61B 34/10* (2016.01)
(Continued)

(52) U.S. Cl.
CPC .............. *A61B 34/20* (2016.02); *A61B 34/10* (2016.02); *A61B 34/25* (2016.02); *A61B 34/30* (2016.02);
(Continued)

(58) Field of Classification Search
None
See application file for complete search history.

(56) References Cited

U.S. PATENT DOCUMENTS 4,559,936 A 12/1985 Hill
5,078,140 A 1/1992 Kwoh
(Continued)

FOREIGN PATENT DOCUMENTS

AU 2049915/19 8/2019
CN 111739644 A 10/2020
(Continued)

OTHER PUBLICATIONS

International Search Report and Written Opinion for International Application No. PCT/US2021/057353, mailed Feb. 11, 2022, 14 pages.
(Continued)

*Primary Examiner* — Charles A Marmor, II
*Assistant Examiner* — Destiny J Cruickshank
(74) *Attorney, Agent, or Firm* — Foley & Lardner LLP

(57) ABSTRACT

A surgical system includes a tracking system configured to obtain data indicative of a pose of a first bone of a joint and a pose of a second bone of the joint, a display device configured to display a graphical user interface, and circuitry configured to determine an acceptable range of flexion angles of the joint for a gap capture step, determine a current flexion angle of the joint based on the data from the tracking system, determine the current flexion angle relative to the acceptable range of flexion angles for the gap capture step, and control the display device to provide, via the graphical user interface, a visualization of the current flexion angle relative to the acceptable range of flexion angles for a gap capture step.

20 Claims, 17 Drawing Sheets

Related U.S. Application Data filed on Apr. 20, 2021, provisional application No. 63/125,468, filed on Dec. 15, 2020.

(51) Int. Cl.

| | |
|---|---|
| *A61B 34/20* | (2016.01) |
| *A61B 34/30* | (2016.01) |
| *A61B 90/00* | (2016.01) |
| A61B 17/02 | (2006.01) |
| A61B 34/35 | (2016.01) |
| A61F 2/46 | (2006.01) |

(52) U.S. Cl.

CPC .............. *A61B 90/06* (2016.02); *A61B 90/39* (2016.02); *A61B 2017/0268* (2013.01); *A61B 2034/102* (2016.02); *A61B 2034/104* (2016.02); *A61B 2034/105* (2016.02); *A61B 2034/2068* (2016.02); *A61B 2034/252* (2016.02); *A61B 34/35* (2016.02); *A61B 2090/064* (2016.02); *A61B 2090/067* (2016.02); *A61B 2090/3916* (2016.02); *A61F 2/46* (2013.01)

(56) References Cited

U.S. PATENT DOCUMENTS

| | | | |
|---|---|---|---|
| 5,413,573 | A | 5/1995 | Koivukangas |
| 5,540,696 | A | 7/1996 | Booth et al. |
| 5,630,431 | A | 5/1997 | Taylor |
| 5,682,886 | A | 11/1997 | Delp et al. |
| 5,800,438 | A | 9/1998 | Tuke et al. |
| 5,824,085 | A | 10/1998 | Sahay et al. |
| 6,328,752 | B1 | 12/2001 | Sjostrom et al. |
| 6,595,997 | B2 | 7/2003 | Axelson et al. |
| 6,685,711 | B2 | 2/2004 | Axelson et al. |
| 6,758,850 | B2 | 7/2004 | Smith et al. |
| 6,827,723 | B2 | 12/2004 | Carson |
| 6,859,661 | B2 | 2/2005 | Tuke |
| 7,008,362 | B2 | 3/2006 | Fitzgibbon |
| 7,412,897 | B2 | 8/2008 | Crottet et al. |
| 7,510,557 | B1 | 3/2009 | Bonutti |
| 7,547,307 | B2 | 6/2009 | Carson et al. |
| 7,591,821 | B2 | 9/2009 | Kelman |
| 7,607,440 | B2 | 10/2009 | Coste-Maniere et al. |
| 7,618,421 | B2 | 11/2009 | Axelson et al. |
| 7,634,306 | B2 | 12/2009 | Sarin et al. |
| 7,670,345 | B2 | 3/2010 | Plassky et al. |
| 7,696,899 | B2 | 4/2010 | Immerz et al. |
| 7,794,467 | B2 | 9/2010 | McGinley et al. |
| 7,831,295 | B2 | 11/2010 | Friedrich et al. |
| 7,927,336 | B2 | 4/2011 | Rasmussen |
| 7,931,655 | B2 | 4/2011 | Axelson et al. |
| 7,945,310 | B2 | 5/2011 | Gattani et al. |
| 7,963,913 | B2 | 6/2011 | Devengenzo et al. |
| 8,007,448 | B2 | 8/2011 | Moctezuma De La Barrera |
| 8,010,180 | B2 | 8/2011 | Quaid et al. |
| 8,038,683 | B2 | 10/2011 | Couture et al. |
| 8,075,317 | B2 | 12/2011 | Youngblood |
| 8,078,440 | B2 | 12/2011 | Otto et al. |
| 8,096,997 | B2 | 1/2012 | Plaskos et al. |
| 8,109,942 | B2 | 2/2012 | Carson |
| 8,116,847 | B2 | 2/2012 | Gattani et al. |
| 8,126,533 | B2 | 2/2012 | Lavallee |
| 8,160,345 | B2 | 4/2012 | Pavlovskaia et al. |
| 8,170,888 | B2 | 5/2012 | Silverman |
| 8,172,775 | B2 | 5/2012 | Warkentine et al. |
| 8,197,549 | B2 | 6/2012 | Amirouche et al. |
| 8,257,360 | B2 | 9/2012 | Richard et al. |
| 8,265,790 | B2 | 9/2012 | Amiot et al. |
| 8,265,949 | B2 | 9/2012 | Haddad |
| 8,277,455 | B2 | 10/2012 | Couture et al. |
| 8,337,508 | B2 | 12/2012 | Lavallee et al. |
| 8,357,111 | B2 | 1/2013 | Caillouette et al. |
| 8,377,129 | B2 | 2/2013 | Fitz et al. |
| 8,382,765 | B2 | 2/2013 | Axelson et al. |
| 8,386,077 | B2 | 2/2013 | Birkenbach et al. |
| 8,480,679 | B2 | 7/2013 | Park et al. |
| 8,483,469 | B2 | 7/2013 | Pavlovskaia et al. |
| 8,521,252 | B2 | 8/2013 | Diez |
| 8,545,509 | B2 | 10/2013 | Park et al. |
| 8,548,559 | B2 | 10/2013 | Hodgson et al. |
| 8,551,023 | B2 | 10/2013 | Sherman et al. |
| 8,551,099 | B2 | 10/2013 | Lang et al. |
| 8,626,267 | B2 | 1/2014 | Lavallee |
| 8,641,726 | B2 | 2/2014 | Bonutti |
| 8,682,052 | B2 | 3/2014 | Fitz et al. |
| 8,707,963 | B2 | 4/2014 | Davis et al. |
| 8,715,291 | B2 | 5/2014 | Park et al. |
| 8,721,568 | B2 | 5/2014 | Rock et al. |
| 8,777,875 | B2 | 7/2014 | Park |
| 8,801,719 | B2 | 8/2014 | Park et al. |
| 8,801,720 | B2 | 8/2014 | Park et al. |
| 8,832,019 | B2 | 9/2014 | Gao |
| 8,834,490 | B2 | 9/2014 | Bonutti |
| 8,845,645 | B2 | 9/2014 | Wilkinson et al. |
| 8,861,818 | B2 | 10/2014 | Ito et al. |
| 8,880,152 | B2 | 11/2014 | Lavallee |
| 8,885,904 | B2 | 11/2014 | Darrow et al. |
| 8,938,282 | B2 | 1/2015 | Daon et al. |
| 8,951,260 | B2 | 2/2015 | Lang et al. |
| 8,956,355 | B2 | 2/2015 | Edwards et al. |
| 8,965,483 | B2 | 2/2015 | Couture et al. |
| 8,974,468 | B2 | 3/2015 | Borja |
| 8,979,859 | B2 | 3/2015 | Leparmentier et al. |
| 9,002,426 | B2 | 4/2015 | Quaid et al. |
| 9,101,394 | B2 | 8/2015 | Arata et al. |
| 9,119,722 | B1 | 9/2015 | Kusuma |
| 9,125,669 | B2 | 9/2015 | Ranawat et al. |
| 9,167,989 | B2 | 10/2015 | Odermatt et al. |
| 9,168,153 | B2 | 10/2015 | Bettenga |
| 9,173,716 | B2 | 11/2015 | Kasodekar et al. |
| 9,186,292 | B2 | 11/2015 | Besendorfer |
| 9,220,510 | B2 | 12/2015 | Cheal et al. |
| 9,237,951 | B1 | 1/2016 | Hakki |
| 9,241,801 | B1 | 1/2016 | Parry et al. |
| 9,247,998 | B2 | 2/2016 | Hladio et al. |
| 9,248,001 | B2 | 2/2016 | Colombet et al. |
| 9,259,290 | B2 | 2/2016 | Jenkins et al. |
| 9,262,802 | B2 | 2/2016 | Aghazadeh |
| 9,265,447 | B2 | 2/2016 | Stein et al. |
| 9,271,756 | B2 | 3/2016 | Van Der Walt et al. |
| 9,277,968 | B2 | 3/2016 | Min et al. |
| 9,286,355 | B2 | 3/2016 | De Guise et al. |
| 9,289,264 | B2 | 3/2016 | Iorgulescu et al. |
| 9,301,812 | B2 | 4/2016 | Kehres et al. |
| 9,332,987 | B2 | 5/2016 | Leimbach et al. |
| 9,406,134 | B2 | 8/2016 | Klingenbeck-Regn |
| 9,433,425 | B2 | 9/2016 | Wilkinson |
| 9,439,656 | B2 | 9/2016 | Chana et al. |
| 9,517,000 | B2 | 12/2016 | Donhowe et al. |
| 9,532,788 | B2 | 1/2017 | Jordan et al. |
| 9,532,838 | B2 | 1/2017 | Coste-Maniere et al. |
| 9,549,742 | B2 | 1/2017 | Berend et al. |
| 9,549,782 | B2 | 1/2017 | Park et al. |
| 9,554,953 | B2 | 1/2017 | Dirauf et al. |
| 9,561,082 | B2 | 2/2017 | Yen et al. |
| 9,572,682 | B2 | 2/2017 | Aghazadeh |
| 9,585,725 | B2 | 3/2017 | Bonutti |
| 9,585,768 | B2 | 3/2017 | Sherman et al. |
| 9,592,133 | B2 | 3/2017 | Toler et al. |
| 9,597,096 | B2 | 3/2017 | Aghazadeh |
| 9,610,086 | B2 | 4/2017 | Park et al. |
| 9,610,134 | B2 | 4/2017 | Kubiak et al. |
| 9,639,156 | B2 | 5/2017 | Iorgulescu et al. |
| 9,684,768 | B2 | 6/2017 | Lavallee et al. |
| 9,700,292 | B2 | 7/2017 | Nawana et al. |
| 9,724,165 | B2 | 8/2017 | Arata et al. |
| 9,737,311 | B2 | 8/2017 | Lavallee et al. |
| 9,737,369 | B2 | 8/2017 | Burger et al. |
| 9,763,683 | B2 | 9/2017 | Bonutti |
| 9,763,746 | B2 | 9/2017 | Deichmann et al. |
| 9,782,226 | B2 | 10/2017 | Park et al. |
| 9,782,229 | B2 | 10/2017 | Crawford et al. |

(56) References Cited

U.S. PATENT DOCUMENTS

| | | | |
|---|---|---|---|
| 9,808,356 B2 | 11/2017 | Haight et al. | |
| 9,848,896 B2 | 12/2017 | Emslie et al. | |
| 9,861,446 B2 | 1/2018 | Lang | |
| 9,888,931 B2 | 2/2018 | Bake | |
| 9,901,404 B2 | 2/2018 | Park et al. | |
| 9,901,463 B2 | 2/2018 | Mahfouz | |
| 9,911,187 B2 | 3/2018 | Steinle et al. | |
| 9,913,691 B2 | 3/2018 | Brooks | |
| 9,913,692 B2 | 3/2018 | Arata et al. | |
| 9,916,421 B2 | 3/2018 | Vorhis et al. | |
| 9,987,092 B2 | 6/2018 | Hladio et al. | |
| 10,010,377 B2 | 7/2018 | Iorgulescu et al. | |
| 10,052,164 B2 | 8/2018 | Overmyer | |
| 10,070,931 B2 | 9/2018 | Itkowitz et al. | |
| 10,070,973 B2 | 9/2018 | Sherman et al. | |
| 10,071,488 B2 | 9/2018 | Robinson et al. | |
| 10,076,344 B2 | 9/2018 | Toler | |
| 10,080,616 B2 | 9/2018 | Wilkinson et al. | |
| 10,092,361 B2 | 10/2018 | Ferro et al. | |
| 10,102,309 B2 | 10/2018 | Mckinnon et al. | |
| 10,117,658 B2 | 11/2018 | Talbot | |
| 10,130,375 B2 | 11/2018 | Yager et al. | |
| 10,136,950 B2 | 11/2018 | Schoenefeld | |
| 10,136,952 B2 | 11/2018 | Couture et al. | |
| 10,172,687 B2 | 1/2019 | Garbus et al. | |
| 10,194,991 B2 | 2/2019 | Bonny et al. | |
| 10,201,320 B2 | 2/2019 | Saget et al. | |
| 10,206,714 B2 | 2/2019 | Van Der Walt et al. | |
| 10,206,792 B2 | 2/2019 | Sherman et al. | |
| 10,226,261 B2 | 3/2019 | Park et al. | |
| 10,226,306 B2 | 3/2019 | Itkowitz et al. | |
| 10,231,739 B1 | 3/2019 | Bonutti | |
| 10,231,786 B2 | 3/2019 | Ferro et al. | |
| 10,238,454 B2 | 3/2019 | Boettner et al. | |
| 10,271,954 B2 | 4/2019 | Roach et al. | |
| 10,272,569 B2 | 4/2019 | Swarup et al. | |
| 10,278,777 B1 | 5/2019 | Lang | |
| 10,285,683 B2 | 5/2019 | Plaskos et al. | |
| 10,307,269 B2 | 6/2019 | Miller | |
| 10,368,947 B2 | 8/2019 | Lang | |
| 10,416,624 B2 | 9/2019 | Bly et al. | |
| 10,420,611 B2 | 9/2019 | Jaramaz et al. | |
| 10,426,556 B2 | 10/2019 | Miga et al. | |
| 10,441,366 B2 | 10/2019 | Tabandeh et al. | |
| 10,441,438 B1 | 10/2019 | Rahman et al. | |
| 10,452,238 B2 | 10/2019 | Nikou et al. | |
| 10,456,075 B2 | 10/2019 | Auchinleck et al. | |
| 10,456,166 B2 | 10/2019 | Cooper et al. | |
| 10,463,242 B2 | 11/2019 | Kesten et al. | |
| 10,470,838 B2 | 11/2019 | Epstein et al. | |
| 10,492,693 B2 | 12/2019 | Irisawa | |
| 10,492,798 B2 | 12/2019 | Metzger | |
| 10,548,667 B2 | 2/2020 | Flett et al. | |
| 10,555,777 B2 | 2/2020 | Griffiths et al. | |
| 10,572,733 B2 | 2/2020 | Wells et al. | |
| 10,575,910 B2 | 3/2020 | Itkowitz et al. | |
| 10,595,880 B2 | 3/2020 | Otto et al. | |
| 10,595,887 B2 | 3/2020 | Shelton et al. | |
| 10,595,952 B2 | 3/2020 | Forrest et al. | |
| 10,610,310 B2 | 4/2020 | Todd et al. | |
| 10,610,315 B2 | 4/2020 | Itkowitz et al. | |
| 10,610,316 B2 | 4/2020 | Swarup et al. | |
| 10,617,479 B2 | 4/2020 | Itkowitz et al. | |
| 10,624,807 B2 | 4/2020 | Itkowitz et al. | |
| 10,638,970 B2 | 5/2020 | Obma et al. | |
| 10,739,963 B2 | 8/2020 | Nikou et al. | |
| 10,765,384 B2 | 9/2020 | Wollowick et al. | |
| 2002/0055918 A1 | 5/2002 | Hlathein et al. | |
| 2004/0260301 A1 | 12/2004 | Lionberger et al. | |
| 2005/0020941 A1 | 1/2005 | Tarabichi | |
| 2005/0113846 A1 | 5/2005 | Carson | |
| 2005/0119661 A1 | 6/2005 | Hodgson et al. | |
| 2005/0149040 A1 | 7/2005 | Haines et al. | |
| 2005/0171545 A1 | 8/2005 | Walsh et al. | |
| 2005/0234466 A1 | 10/2005 | Stallings | |
| 2005/0251148 A1 | 11/2005 | Friedrich et al. | |
| 2006/0015120 A1 | 1/2006 | Richard et al. | |
| 2006/0064043 A1 | 3/2006 | Goeggelmann et al. | |
| 2006/0200026 A1 | 9/2006 | Wallace et al. | |
| 2006/0241405 A1 | 10/2006 | Leitner et al. | |
| 2007/0073136 A1 | 3/2007 | Metzger | |
| 2007/0123896 A1 | 5/2007 | Wyss et al. | |
| 2007/0179626 A1 | 8/2007 | De La Barrera et al. | |
| 2007/0244488 A1 | 10/2007 | Metzger et al. | |
| 2008/0208081 A1 | 8/2008 | Murphy et al. | |
| 2008/0249394 A1 | 10/2008 | Giori et al. | |
| 2008/0262812 A1* | 10/2008 | Arata | A61B 90/36 703/11 |
| 2008/0281301 A1 | 11/2008 | DeBoer et al. | |
| 2008/0281328 A1 | 11/2008 | Lang et al. | |
| 2008/0281426 A1 | 11/2008 | Fitz et al. | |
| 2009/0209884 A1* | 8/2009 | Van Vorhis | G16H 50/50 600/595 |
| 2010/0063508 A1 | 3/2010 | Borja et al. | |
| 2010/0064216 A1 | 3/2010 | Borja et al. | |
| 2010/0145344 A1 | 6/2010 | Jordan et al. | |
| 2011/0029091 A1 | 2/2011 | Bojarski et al. | |
| 2011/0071528 A1 | 3/2011 | Carson | |
| 2011/0071530 A1 | 3/2011 | Carson | |
| 2011/0304332 A1 | 12/2011 | Mahfouz | |
| 2011/0306986 A1 | 12/2011 | Lee et al. | |
| 2012/0143084 A1 | 6/2012 | Shoham | |
| 2012/0176306 A1 | 7/2012 | Lightcap et al. | |
| 2012/0226198 A1 | 9/2012 | Carson | |
| 2012/0226481 A1 | 9/2012 | Carson | |
| 2013/0072821 A1 | 3/2013 | Odermatt et al. | |
| 2013/0085510 A1 | 4/2013 | Stefanchik et al. | |
| 2013/0144570 A1 | 6/2013 | Axelson et al. | |
| 2013/0209953 A1 | 8/2013 | Arlinsky et al. | |
| 2014/0031664 A1 | 1/2014 | Kang et al. | |
| 2014/0039520 A1 | 2/2014 | Haider et al. | |
| 2014/0073907 A1 | 3/2014 | Kumar et al. | |
| 2014/0108983 A1 | 4/2014 | William R. et al. | |
| 2014/0128727 A1 | 5/2014 | Daon et al. | |
| 2014/0135791 A1 | 5/2014 | Nikou et al. | |
| 2014/0188240 A1 | 7/2014 | Lang et al. | |
| 2014/0189508 A1 | 7/2014 | Granchi et al. | |
| 2014/0296871 A1 | 10/2014 | Chen et al. | |
| 2015/0105782 A1 | 4/2015 | D'Lima et al. | |
| 2015/0106024 A1 | 4/2015 | Lightcap et al. | |
| 2016/0022374 A1 | 1/2016 | Haider et al. | |
| 2016/0220175 A1 | 8/2016 | Tam et al. | |
| 2016/0278754 A1 | 9/2016 | Todorov et al. | |
| 2016/0278868 A1 | 9/2016 | Berend et al. | |
| 2016/0338777 A1 | 11/2016 | Penenberg et al. | |
| 2016/0354161 A1 | 12/2016 | Deitz | |
| 2017/0014169 A1 | 1/2017 | Dean et al. | |
| 2017/0042557 A1 | 2/2017 | Plaskos et al. | |
| 2017/0061375 A1 | 3/2017 | Laster et al. | |
| 2017/0196571 A1 | 7/2017 | Berend et al. | |
| 2017/0258532 A1 | 9/2017 | Shalayev et al. | |
| 2017/0312099 A1 | 11/2017 | Paszicsnyek | |
| 2017/0325973 A1 | 11/2017 | Bonny et al. | |
| 2017/0340389 A1 | 11/2017 | Otto et al. | |
| 2017/0347922 A1 | 12/2017 | Bhandari | |
| 2017/0348008 A1 | 12/2017 | Lavallee et al. | |
| 2018/0064496 A1 | 3/2018 | Hladio et al. | |
| 2018/0071049 A1 | 3/2018 | Nowatschin et al. | |
| 2018/0085135 A1 | 3/2018 | Singh et al. | |
| 2018/0116805 A1 | 5/2018 | Johannaber et al. | |
| 2018/0116823 A1 | 5/2018 | Johannaber et al. | |
| 2018/0132940 A1 | 5/2018 | Kao et al. | |
| 2018/0132949 A1 | 5/2018 | Merette et al. | |
| 2018/0168750 A1 | 6/2018 | Staunton et al. | |
| 2018/0168762 A1 | 6/2018 | Scheib et al. | |
| 2018/0177512 A1 | 6/2018 | Hogan et al. | |
| 2018/0199995 A1 | 7/2018 | Odermatt et al. | |
| 2018/0214180 A1 | 8/2018 | Theodore et al. | |
| 2018/0256256 A1 | 9/2018 | May et al. | |
| 2018/0317898 A1 | 11/2018 | Plaskos et al. | |
| 2018/0338796 A1 | 11/2018 | Yao et al. | |
| 2018/0344409 A1 | 12/2018 | Bonny et al. | |
| 2018/0368930 A1 | 12/2018 | Esterberg et al. | |
| 2019/0000631 A1 | 1/2019 | Blankevoort et al. | |

(56) References Cited

U.S. PATENT DOCUMENTS

| | | |
|---|---|---|
| 2019/0008599 A1 | 1/2019 | Lynch et al. |
| 2019/0066832 A1 | 2/2019 | Kang et al. |
| 2019/0069962 A1 | 3/2019 | Tabandeh et al. |
| 2019/0069963 A1 | 3/2019 | Azizian et al. |
| 2019/0083191 A1 | 3/2019 | Gilhooley et al. |
| 2019/0090952 A1 | 3/2019 | Bonny et al. |
| 2019/0090962 A1 | 3/2019 | Boettner |
| 2019/0099228 A1 | 4/2019 | Keller et al. |
| 2019/0117156 A1 | 4/2019 | Howard et al. |
| 2019/0117407 A1 | 4/2019 | Yang |
| 2019/0122330 A1 | 4/2019 | Saget et al. |
| 2019/0133695 A1 | 5/2019 | Hladio et al. |
| 2019/0147128 A1 | 5/2019 | O'Connor |
| 2019/0175283 A1 | 6/2019 | Bonny et al. |
| 2019/0200900 A1 | 7/2019 | Thelen et al. |
| 2019/0201101 A1 | 7/2019 | Hafez |
| 2019/0201214 A1 | 7/2019 | Miller et al. |
| 2019/0209079 A1 | 7/2019 | Delport |
| 2019/0216520 A1 | 7/2019 | Babak et al. |
| 2019/0223962 A1 | 7/2019 | Roldan et al. |
| 2019/0224016 A1 | 7/2019 | Walker et al. |
| 2019/0240045 A1 | 8/2019 | Couture |
| 2019/0240046 A1 | 8/2019 | Couture |
| 2019/0254756 A1 | 8/2019 | Zhang et al. |
| 2019/0272917 A1 | 9/2019 | Couture et al. |
| 2019/0274662 A1 | 9/2019 | Rockman et al. |
| 2019/0274762 A1 | 9/2019 | Kim et al. |
| 2019/0290198 A1 | 9/2019 | Belson et al. |
| 2019/0311542 A1 | 10/2019 | Douglas et al. |
| 2019/0325386 A1 | 10/2019 | Laster et al. |
| 2019/0336220 A1 | 11/2019 | Hladio et al. |
| 2019/0365481 A1 | 12/2019 | Otto et al. |
| 2019/0374130 A1 | 12/2019 | Bydlon et al. |
| 2019/0380792 A1 | 12/2019 | Poltaretskyi et al. |
| 2019/0388153 A1 | 12/2019 | Running et al. |
| 2019/0388157 A1 | 12/2019 | Shameli et al. |
| 2020/0000400 A1 | 1/2020 | Mckinnon et al. |
| 2020/0015598 A1 | 1/2020 | Hondori et al. |
| 2020/0060772 A1 | 2/2020 | Konh et al. |
| 2020/0060773 A1 | 2/2020 | Barral et al. |
| 2020/0100848 A1 | 4/2020 | Zuhars et al. |
| 2020/0113583 A1 | 4/2020 | Philipp et al. |
| 2020/0305978 A1 | 10/2020 | Tan et al. |
| 2020/0352529 A1 | 11/2020 | Wollowick et al. |
| 2021/0059656 A1 | 3/2021 | Otto et al. |
| 2021/0192759 A1 | 6/2021 | Lang |
| 2021/0216822 A1 | 7/2021 | Paik et al. |
| 2022/0172818 A1 | 6/2022 | Fanson et al. |

FOREIGN PATENT DOCUMENTS

| | | |
|---|---|---|
| EP | 1 518 501 A2 | 3/2005 |
| EP | 1 690 503 A1 | 8/2006 |
| EP | 1 226 788 B1 | 10/2006 |
| EP | 1 755 466 B1 | 12/2007 |
| EP | 2 007 291 A2 | 12/2008 |
| EP | 2 156 794 A1 | 2/2010 |
| EP | 2 384 714 A1 | 11/2011 |
| EP | 1 919 390 B1 | 12/2012 |
| EP | 1 841 372 B1 | 9/2017 |
| EP | 3 334 383 B1 | 4/2020 |
| WO | WO-95/31148 A1 | 11/1995 |
| WO | WO-2004/070580 A2 | 8/2004 |
| WO | WO-2006/078236 A1 | 7/2006 |
| WO | WO-2007/092841 A1 | 8/2007 |
| WO | WO-2012/082164 A1 | 6/2012 |
| WO | WO-2012/082615 A2 | 6/2012 |
| WO | WO-2012/101286 A1 | 8/2012 |
| WO | WO-2015/057814 A1 | 4/2015 |
| WO | WO-2016/146768 A1 | 9/2016 |
| WO | WO-2016/198844 A1 | 12/2016 |
| WO | WO-2017/076886 A1 | 5/2017 |
| WO | WO-2017/108776 A1 | 6/2017 |
| WO | WO-2017/115235 A1 | 7/2017 |
| WO | WO-2017/124043 A1 | 7/2017 |
| WO | WO-2017/147596 A1 | 8/2017 |
| WO | WO-2017/179075 A1 | 10/2017 |
| WO | WO-2018/085694 A1 | 5/2018 |
| WO | WO-2018/085900 A1 | 5/2018 |
| WO | WO-2018/095499 A1 | 5/2018 |
| WO | WO-2018/104704 A1 | 6/2018 |
| WO | WO-2018/161120 A1 | 9/2018 |
| WO | WO-2019/006370 A1 | 1/2019 |
| WO | WO-2019/032828 A2 | 2/2019 |
| WO | WO-2019/068194 A1 | 4/2019 |
| WO | WO-2019/079634 A1 | 4/2019 |
| WO | WO-2019/081915 A1 | 5/2019 |
| WO | WO-2019/135805 A1 | 7/2019 |
| WO | WO-2019/148154 A1 | 8/2019 |
| WO | WO-2019/191722 A1 | 10/2019 |
| WO | WO-2019/224745 A1 | 11/2019 |
| WO | WO-2019/241516 A1 | 12/2019 |
| WO | WO-2019/245849 A1 | 12/2019 |
| WO | WO-2019/245851 A1 | 12/2019 |
| WO | WO-2020/033568 A2 | 2/2020 |
| WO | WO-2020/056443 A1 | 3/2020 |
| WO | WO-2020/065209 A1 | 4/2020 |
| WO | WO-2020/227832 A1 | 11/2020 |

OTHER PUBLICATIONS

Roche, Robotic and Sensor-Assisted Technologies in Knee Arthroplasty,, Holy Cross Hospital Orthopedic Institute, Operative Techniques in Orthopaedics, pp. 127-147 (Year: 2015).

* cited by examiner

300

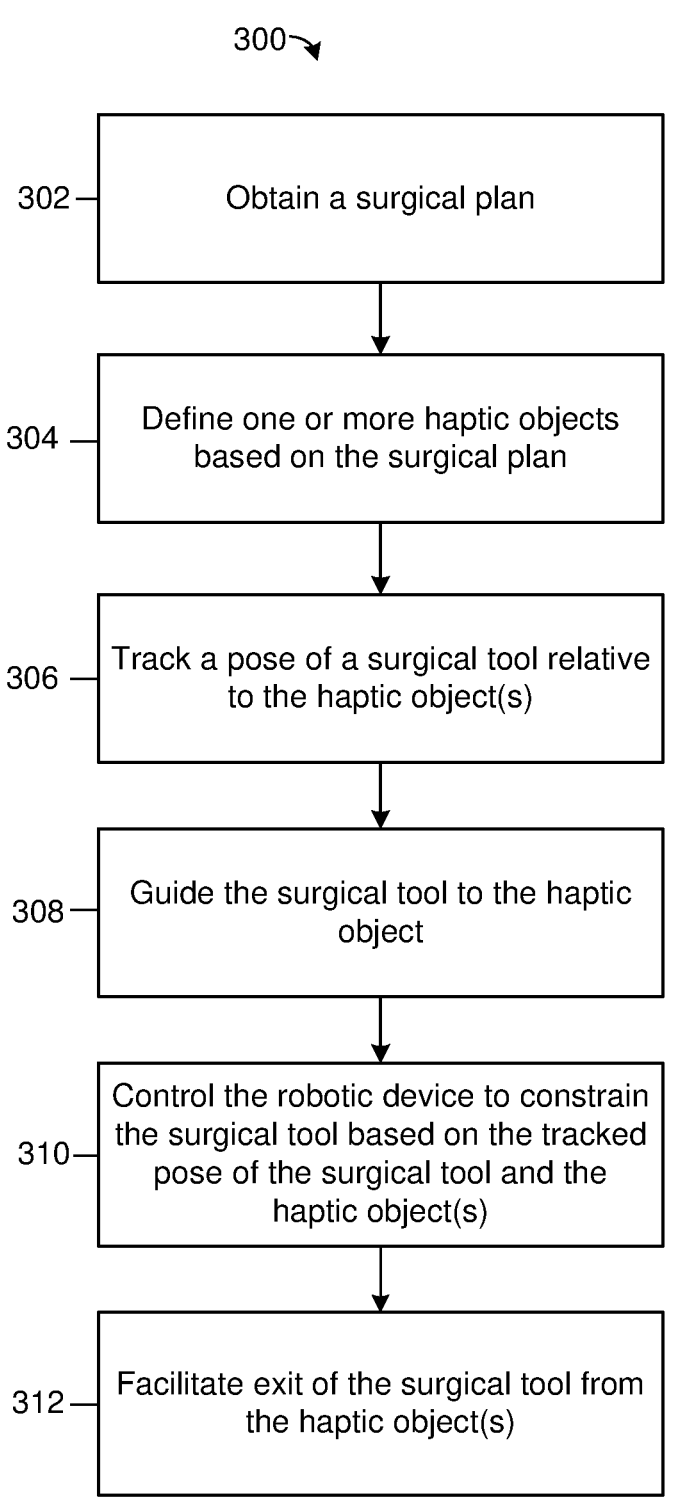

302 — Obtain a surgical plan

304 — Define one or more haptic objects based on the surgical plan

306 — Track a pose of a surgical tool relative to the haptic object(s)

308 — Guide the surgical tool to the haptic object

310 — Control the robotic device to constrain the surgical tool based on the tracked pose of the surgical tool and the haptic object(s)

312 — Facilitate exit of the surgical tool from the haptic object(s)

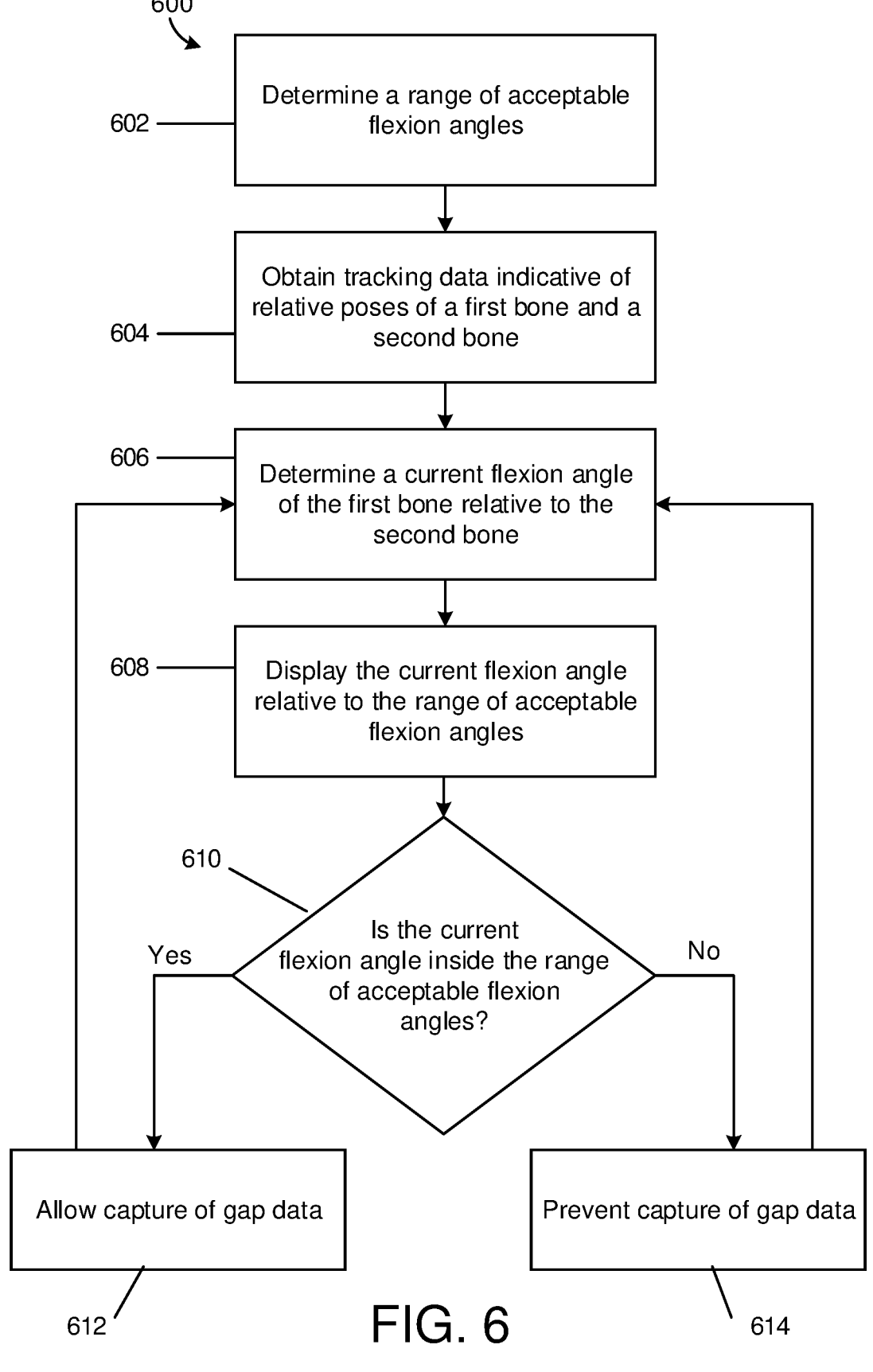

602 — Determine a range of acceptable flexion angles

604 — Obtain tracking data indicative of relative poses of a first bone and a second bone 606 — Determine a current flexion angle of the first bone relative to the second bone 608 — Display the current flexion angle relative to the range of acceptable flexion angles 610 — Is the current flexion angle inside the range of acceptable flexion angles?

Yes

No

Allow capture of gap data

Prevent capture of gap data

1202 —— Obtain a distraction force measurement

1204 — Is the distraction force measurement less than a threshold distraction force measurement?

Yes

No

Allow capture of gap data

Prevent capture of gap data

1206

1208

DYNAMIC GAP CAPTURE AND FLEXION WIDGET

CROSS-REFERENCE TO RELATED APPLICATIONS

This application claims the benefit of and priority to U.S. Provisional Patent Application No. 63/125,468 filed Dec. 15, 2020, U.S. Provisional Patent Application No. 63/177,034 filed Apr. 20, 2021, and U.S. Provisional Patent Application No. 63/226,858 filed Jul. 29, 2021, the entire disclosures of which are incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to assist the surgeon during implementation of the surgical plan. Various features enabling improved planning, improved intra-operative assessments of the patient biomechanics, intraoperative plan adjustments, etc. for use with robotically-assisted surgical systems or other computer-assisted surgical systems may be advantageous.

SUMMARY

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

One implementation of the present disclosure is a surgical system. The surgical system includes a tracking system configured to obtain data indicative of a pose of a first bone of a joint and a pose of a second bone of the joint, a display device configured to display a graphical user interface, and circuitry. The circuitry is configured to determine an acceptable range of flexion angles of the joint for a gap capture step, determine a current flexion angle of the joint based on the data from the tracking system, determine the current flexion angle relative to the acceptable range of flexion angles for the gap capture step, and control the display device to provide, via the graphical user interface, a visualization of the current flexion angle relative to the acceptable range of flexion angles for a gap capture step. The circuitry may also be configured to determine whether the current flexion angle is inside the acceptable range of flexion angles for a gap capture step, and in response to determining the current flexion angle is outside the acceptable range of flexion angles for the gap capture step, prevent the gap capture step. The circuitry may also be configured to determine whether the current flexion angle is inside the acceptable range of flexion angles for a gap capture step, and in response to determining the current flexion angle is inside the acceptable range of flexion angles for the gap capture step, provide a first gap measurement by determining, based on the data from the tracking system, a first gap between the first bone and the second bone achieved during the duration of a first gap capture step.

Another implementation of the present disclosure is a method of controlling a surgical system. The method includes obtaining a surgical plan comprising a plurality of planned measurements, obtaining tracking data indicative of a pose of a first bone of a joint and a pose of a second bone of the joint from a tracking system, determining an acceptable range of flexion angles of the joint for a gap capture step, determining a current flexion angle of the joint based on the tracking data from the tracking system, determining the current flexion angle relative to the acceptable range of flexion angles for the gap capture step, and instructing a display to display, via a graphical user interface, a visualization of the current flexion angle relative to the acceptable range of flexion angles for the gap capture step. The method may also include determining whether the current flexion angle is inside the acceptable range of flexion angles for a gap capture step, and in response to determining the current flexion angle is outside the acceptable range of flexion angles for the gap capture step, prevent the gap capture step. The method may also include determining whether the current flexion angle is inside the acceptable range of flexion angles for a gap capture step, and in response to determining the current flexion angle is inside the acceptable range of flexion angles for the gap capture step, providing a first gap measurement by determining, based on the tracking data from the tracking system, a first gap between the first bone and the second bone achieved during the duration of a first gap capture step.

Another implementation of the present disclosure is one or more non-transitory computer-readable media storing program instructions that, when executed by one or more processors, causes the one or more processors to perform operations relating to controlling a surgical system. The operations include obtaining a surgical plan comprising a plurality of planned measurements, obtaining tracking data indicative of a pose of a first bone of a joint and a pose of a second bone of the joint from a tracking system, determining an acceptable range of flexion angles of the joint for a gap capture step, determining a current flexion angle of the joint based on the tracking data from the tracking system, determining the current flexion angle relative to the acceptable range of flexion angles for the gap capture step, and providing a graphical user interface, which comprises providing a visualization of the current flexion angle relative to the acceptable range of flexion angles for the gap capture step.

BRIEF DESCRIPTION OF THE DRAWINGS

FIG. 3 is a flowchart of a first process that can be executed by the surgical system of FIG. 2, according to an exemplary embodiment.

FIG. 6 is a flowchart of a first process that can be executed by the surgical system of FIG. 5, according to an exemplary embodiment.

DETAILED DESCRIPTION

Figure 1:
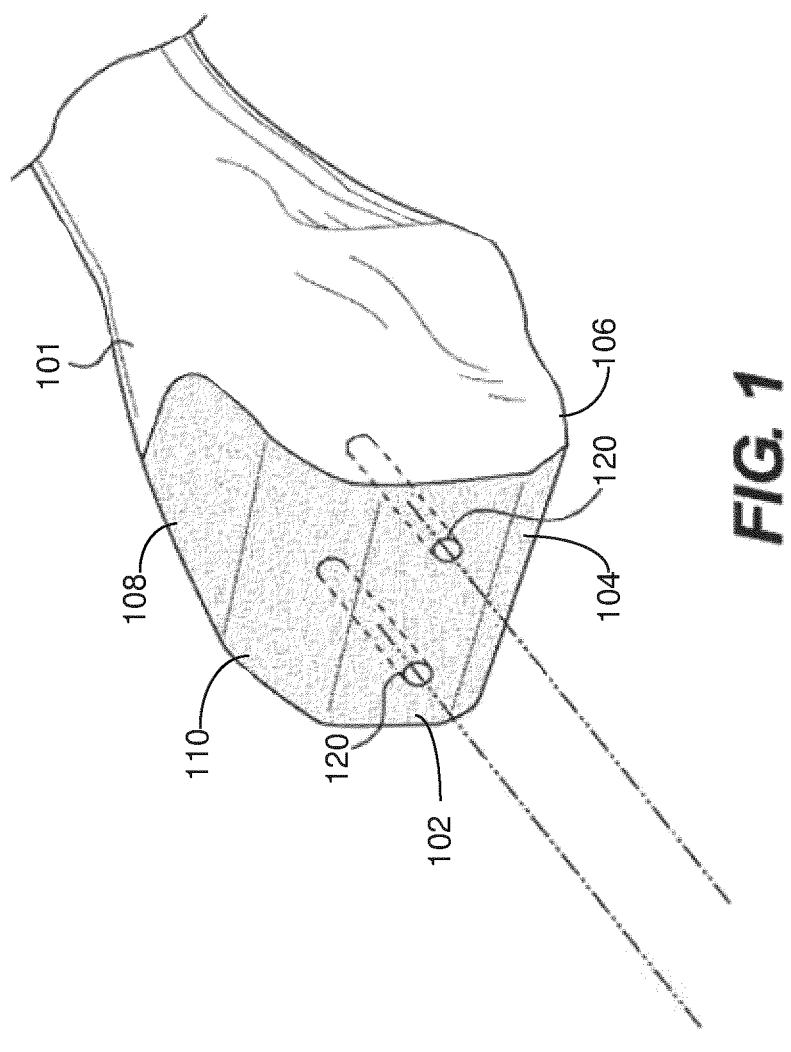
FIG. 1 is a perspective view of a femur prepared to receive an implant component, according to an exemplary embodiment.

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 101 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical tool, for example a surgical tool coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical tool to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical tool as described below. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical tool to create the pilot holes 120 with a high degree of accuracy may improve the outcome of a joint replacement procedure.

A tibia may also be modified during a joint replacement procedure. For example, a planar surface may be created on the tibia at the knee joint to prepare the tibia to mate with a tibial implant component. In some embodiments, one or more pilot holes or other recess (e.g., fin-shaped recess) may also be created in the tibia to facilitate secure coupling of an implant component to the bone.

In some embodiments, the systems and methods described herein provide robotic assistance for creating the planar surfaces 102-110 and the pilot holes 120 at the femur, and/or a planar surface and/or pilot holes 120 or other recess on a tibia. It should be understood that the creation of five planar cuts and two cylindrical pilot holes as shown in FIG. 1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

The positions and orientations of the planar surfaces 102-110, pilot holes 120, and any other surfaces or recesses created on bones of the knee joint can affect how well implant components mate to the bone as well as the resulting biomechanics for the patient after completion of the surgery.

Tension on soft tissue can also be affected. Accordingly, systems and methods for planning the cuts which create these surfaces, facilitating intra-operative adjustments to the surgical plan, and providing robotic-assistance or other guidance for facilitating accurate creation of the planar surfaces 102-110, other surfaces, pilot holes 120, or other recesses can make surgical procedures easier and more efficient for healthcare providers and improve surgical outcomes.

Figure 2:
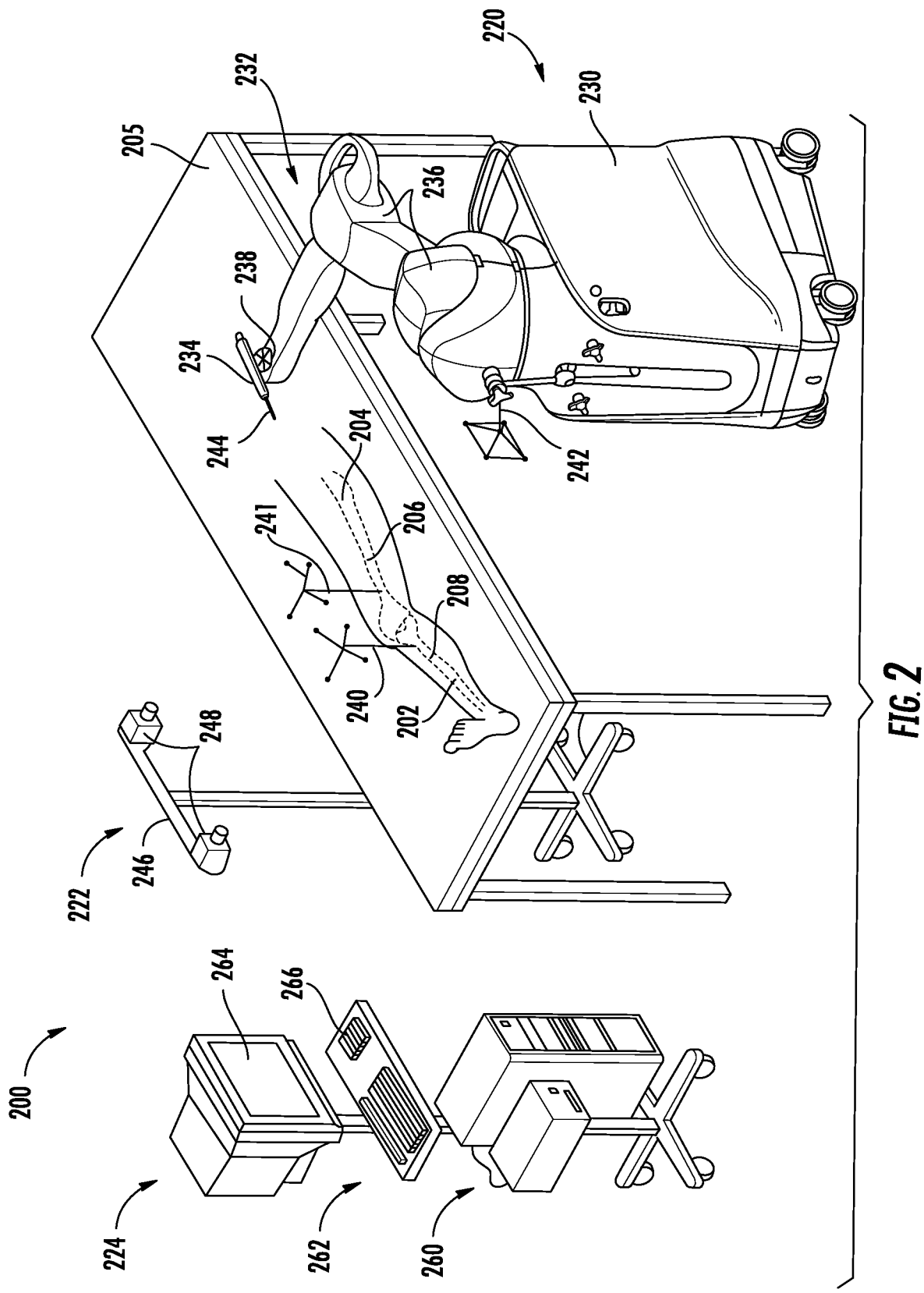
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, e.g., the femur and the pelvis of the patient. Additionally, in still other scenarios, the surgical system 200 is set up to treat a shoulder of a patient, e.g., to facilitate replacement and/or augmentation of components of a shoulder joint (e.g., to facilitate placement of a humeral component, a glenoid component, and a graft or implant augment). Various other anatomical regions and procedures are also possible.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2, the surgical tool 234 includes a spherical burr 244. In other examples, the surgical tool may also be a sagittal saw, for example, with a blade aligned parallel with a tool axis or perpendicular to the tool axis. The surgical tool may also be a drill, for example with a rotary bit aligned parallel with a tool axis or perpendicular to the tool axis. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup implant to facilitate fixation of the cup implant to a pelvis in a planned location and orientation.

Tracking system 222 is configured to track the patient's anatomy (e.g., femur 206 and tibia 208) and the robotic device 220 (e.g., surgical tool 234 and/or robotic arm 232) to enable control of the surgical tool 234 coupled to the robotic arm 232, to determine a position and orientation of modifications or other results made by the surgical tool 234, and to allow a user to visualize the bones (e.g., femur 206, the tibia 208, pelvis, humerus, scapula, etc. as applicable in various procedures), the surgical tool 234, and/or the robotic arm 232 on a display of the computing system 224. The tracking system 222 can also be used to collect biomechanical measurements relating to the patient's anatomy, assess joint gap distances, identify a hip center point, assess native or corrected joint deformities, or otherwise collect information relating to the relative poses of anatomical features. More particularly, the tracking system 222 determines a position and orientation (e.g., pose) of objects (e.g., surgical tool 234, femur 206) with respect to a coordinate frame of reference and tracks (e.g., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials attachable to surgical tool 234, and a detection device 246 configured to detect the three-dimensional position of fiducials (e.g., markers on fiducial trees 240-242). Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). In some embodiments, the markers are active light emitting diodes. A stereoscopic arrangement of cameras 248 on detection device 246 allows the position of each fiducial to be determined in 3D-space through a triangulation approach in the example shown. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (e.g., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262. Computing system 224 may include circuitry configured to enable the operations described herein, for example using processing circuit 260 and/or input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MM), and/or ultrasound. The imaging data is then segmented (e.g., the regions in the imaging corresponding to different anatomical features are distinguished) to obtain the virtual bone model. For example, MM-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans. In some embodiments, the processing circuit facilitates intraoperative modifications to the preoperative plant.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device to control the robotic device to move within the control object (e.g., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. Where one HIP is used to virtually represent a surgical tool, the HIP may be referred to herein as a tool center point (TCP). If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to a "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (e.g., to femur 206). Registration allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (e.g., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, and surgical approach trajectories, etc. defined by the surgical plan. The haptic objects can be oriented and positioned in three-dimensional space relative to a tracked position of a patient's anatomy.

At step 306, a pose of a surgical tool is tracked relative to the haptic object(s), for example by the tracking system 222 described above. In some embodiments, one point on the surgical tool is tracked. In other embodiments, (e.g., in the example of FIGS. 4-5) two points on the surgical tool are tracked, for example a tool center point (TCP) at a tip/effective end of the surgical tool and a second interaction point (SIP) positioned along a body or handle portion of the surgical tool. In other embodiments, three or more points on the surgical tool are tracked. A pose of the surgical tool is ascertained relative to a coordinate system in which the one or more haptic objects are defined and, in some embodiments, in which the pose of one or more anatomical features of the patient is also tracked.

At step 308, the surgical tool is guided to the haptic object(s). For example, the display 264 of the surgical system 200 may display a graphical user interface instructing a user on how (e.g., which direction) to move the surgical tool and/or robotic device to bring the surgical tool to a haptic object. As another example, the surgical tool may be guided to a haptic object using a collapsing haptic boundary as described in U.S. Pat. No. 9,289,264, the entire disclosure of which is incorporated by reference herein. As another example, the robotic device may be controlled to automatically move the surgical tool to a haptic object.

In an embodiment where the robotic device is controlled to automatically move the surgical tool to the haptic object (referred to as motorized alignment or automated alignment), the robotic device may be controlled so that a duration of the alignment is bounded by preset upper and lower time thresholds. That is, across various instances of process 300 and multiple procedures, automated alignment in step 308 may be configured to always take between a first amount of time (the lower time threshold) and a second amount of time (the upper time threshold). The lower time threshold may be selected such that the robotic device moves over a long enough duration to be perceived as well-controlled and to minimize collision or other risks associated with high speed. The upper time threshold may be selected such that the robotic device moves over a short enough duration to avoid user impatience and provide improved usability. For example, the upper time threshold hold may be approximately five seconds in an example where the lower time thresholds is approximately three seconds. In other embodiments, a single duration setpoint is used (e.g., four seconds). Step 308 can include optimizing a path for the robotic device such that the step 308 ensures successful alignment to the haptic object while also satisfying the upper and lower time thresholds or duration setpoint.

At step 310, the robotic device is controlled to constrain movement of the surgical tool based on the tracked pose of the surgical tool and the poses of one or more haptic objects. The constraining of the surgical tool may be achieved as described above with reference to FIG. 2.

At step 312, exit of the surgical tool from the haptic object(s) is facilitated, e.g., to release the constraints of a haptic object. For example, in some embodiments, the robotic device is controlled to allow the surgical tool to exit a haptic object along an axis of the haptic object. In some embodiments, the surgical tool may be allowed to exit the haptic object in a pre-determined direction relative to the haptic object. The surgical tool may thereby be removed from the surgical field and the haptic object allowed to facilitate subsequent steps of the surgical procedure. Additionally, it should be understood that, in some cases, the process 300 may return to step 308 where the surgical tool is guided to the same or different haptic object after exiting a haptic object at step 312.

Process 300 may thereby be executed by the surgical system 200 to facilitate a surgical procedure. Features of process 300 are shown in FIGS. 4-8 below according to some embodiments, and such features can be combined in various combinations in various embodiments and/or based on settings selected for a particular procedure. Furthermore, it should be understood that the features of FIGS. 4-8 may be provided while omitting some or all other steps of process 300. All such possibilities are within the scope of the present disclosure.

Figure 4:
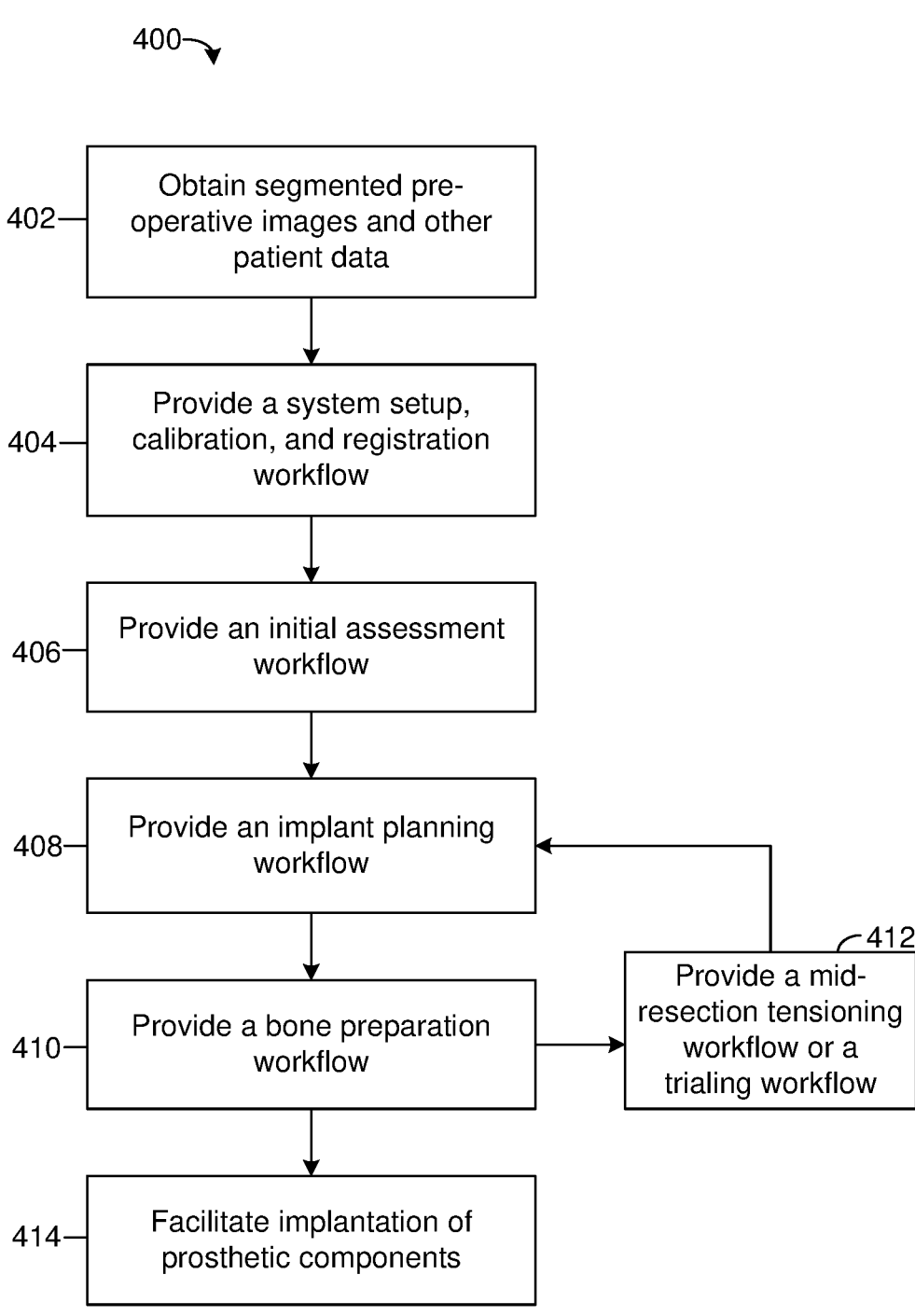
FIG. 4 is a flowchart of a second process that can be executed by the surgical system of FIG. 2, according to an exemplary embodiment.

Referring now to FIG. 4, a flowchart of a process 400 for facilitating surgical planning and guidance is shown, according to an exemplary embodiment. The process 400 may be executed by the surgical system 200 of FIG. 2, in some embodiments. In some cases, the process 300 is executed as part of executing the process 400.

At step 402, segmented pre-operative images and other patient data are obtained, for example by the surgical system 200. For example, segmented pre-operative CT images or MRI images may be received at the computing system 224 from an external server. In some cases, pre-operative images of a patient's anatomy are collected using an imaging device and segmented by a separate computing system and/or with manual user input to facilitate segmentation. In other embodiments, unsegmented pre-operative images are received at the computing system 224 and the computing system 224 is configured to automatically segment the images. The segmented pre-operative images can show the geometry, shape, size, density, and/or other characteristics of bones of a joint which is to be operated on in a procedure performed using process 400.

Other patient data can also be obtained at step 402. For example, the computing system 224 may receive patient information from an electronic medical records system. As another example, the computing system 224 may accept user input of patient information. The other patient data may include a patient's name, identification number, biographical information (e.g., age, weight, etc.), other health conditions, etc. In some embodiments, the patient data obtained at step 402 includes information specific to the procedure to be performed and the relevant pre-operative diagnosis. For example, the patient data may indicate which joint the procedure will be performed on (e.g., right knee, left knee). The patient data may indicate a diagnosed deformity, for example indicating whether a knee joint was diagnosed as having a varus deformity or a valgus deformity. This or other data that may facilitate the surgical procedure may be obtained at step 402.

At step 404, a system setup, calibration, and registration workflow is provided, for example by the surgical system 200. The system setup, calibration, and registration workflows may be configured to prepare the surgical system 200 for use in facilitating a surgical procedure. For example, at step 404, the computing system 224 may operate to provide graphical user interfaces that include instructions for performing system setup, calibration, and registration steps. The computing system 224 may also cause the tracking system 222 to collect tracking data and control the robotic device 220 to facilitate system setup, calibration, and/or registration. The computing system 224 may also receiving tracking data from the tracking system 222 and information from the computing system 224 and use the received information and data to calibrate the robotic device 220 and define various geometric relationships between tracked points (e.g., fiducials, markers), other components of the surgical system 200 (e.g., robotic arm 232, surgical tool 234, probe), and virtual representations of anatomical features (e.g., virtual bone models).

The system setup workflow provided at step 404 may include guiding the robotic device 220 to a position relative to a surgical table and the patient which will be suitable for completing an entire surgical procedure without repositioning the robotic device 220. For example, the computing system 224 may generate and provide a graphical user interface configured to provide instructions for moving a portable cart of the robotic device 220 into a preferred position. In some embodiments, the robotic device 220 can be tracked to determine whether the robotic device 220 is properly positioned. Once the cart is positioned, in some embodiments the robotic device 220 is controlled to automatically position the robotic arm 232 in a pose suitable for initiation of calibration and/or registration workflows.

The calibration and registration workflows provided at step 404 may include generating instructions for a user to perform various calibration and registration tasks while operating the tracking system 222 to generate tracking data. The tracking data can then be used to calibrate the tracking system 222 and the robotic device 220 and to register the first fiducial tree 240, second fiducial tree 241, and third fiducial tree 242 relative to the patient's anatomical features, for example by defining geometric relationships between the fiducial trees 240-242 and relevant bones of the patient in the example of FIG. 2. The registration workflow may include tracking a probe used to touch various points on the bones of a joint. In some embodiments, providing the registration workflow may include providing instructions to couple a checkpoint (e.g., a screw or pin configured to be contacted by a probe) to a bone and tracking a probe as the probe contacts the checkpoint and as the probe is used to paint (e.g., move along, touch many points along) one or more surfaces of the bone. The probe can be moved and tracked in order to collect points in or proximate the joint to be operated upon as well as at other points on the bone (e.g., at an ankle or hip for a knee surgery).

In some embodiments, providing the registration workflow includes generating instructions to move the patient's leg to facilitate collection of relevant tracking data that can be used to identify the location of a biomechanical feature, for example a hip center point. Providing the registration workflow can include providing audio or visual feedback indicating whether the leg was moved in the proper manner to collect sufficient tracking data. Various methods and approaches for registration and calibration can be used in various embodiments. Step 404 may include steps performed before or after an initial surgical incision is made in the patient's skin to initiate the surgical procedure.

At step 406, an initial assessment workflow is provided, for example by the surgical system 200. The initial assessment workflow provides an initial assessment of the joint to be operated upon based on tracked poses of the bones of the joint. For example, the initial assessment workflow may include tracking relative positions of a tibia and a femur using data from the tracking system while providing real-time visualizations of the tibia and femur via a graphical user interface. The computing system 224 may provide instructions via the graphical user interface to move the tibia and femur to different relative positions (e.g., different degrees of flexion) and to exert different forces on the joint (e.g., a varus or valgus force). In some embodiments, the initial assessment workflow includes determining, by the surgical system 200 and based on data from the tracking system 222, whether the patient's joint has a varus or valgus deformity, and, in some embodiments, determining a magnitude of the deformity. In some embodiments, the initial assessment workflow may include collecting data relating to native ligament tension or native gaps between bones and/or implant components of the joint. In some embodiments, the initial assessment workflow may include displaying instructions to exert a force on the patient's leg to place the joint in a corrected state corresponding to a desired outcome for a joint arthroplasty procedure, and recording the relative poses of the bones and other relevant measurements while the joint is in the corrected state. The initial assessment workflow thereby results in collection of data that may be useful for the surgical system 200 or a surgeon in later steps of process 400.

At step 408, an implant planning workflow is provided, for example, by the surgical system 200. The implant planning workflow is configured to facilitate users in planning implant placement relative to the patient's bones and/or planning bone cuts or other modifications for preparing bones to receive implant components. Step 408 may include generating, for example by the computing system 224, three-dimensional computer models of the bones of the joint (e.g., a tibia model and a femur model) based on the segmented medical images received at step 402. Step 408 may also include obtaining three-dimensional computer models of prosthetic components to be implanted at the joint (e.g., a tibial implant model and a femoral implant model). A graphical user interface can be generated showing multiple views of the three-dimensional bone models with the three-dimensional implant models shown in planned positions relative to the three-dimensional bone models. Providing the implant planning workflow can include enabling the user to adjust the position and orientation of the implant models relative to the bone models. Planned cuts for preparing the bones to allow the implants to be implanted at the planned positions can then be automatically based on the positioning of the implant models relative to the bone models.

The graphical user interface can include data and measurements from pre-operative patient data (e.g., from step 402) and from the initial assessment workflow (step 406) and/or related measurements that would result from the planned implant placement. The planned measurements (e.g., planned gaps, planned varus/valgus angles, etc.) can be calculated based in part on data collected via the tracking system 222 in other phases of process 400, for example from the initial assessment in step 406 or trialing or tensioning workflows described below with reference to step 412.

The implant planning workflow may also include providing warnings (alerts, notifications) to users when an implant plan violates various criteria. In some cases, the criteria can be predefined, for example, related to regulatory or system requirements that are constant for all surgeons and/or for all patients. In other embodiments, the criteria may be related to surgeon preferences, such that the criteria for triggering a warning can be different for different surgeons. In some cases, the computing system 224 can prevent the process 400 from moving out of the implant planning workflow when one or more of certain criteria are not met.

The implant planning workflow provided at step 408 thereby results in planned cuts for preparing a joint to receive prosthetic implant components. In some embodiments, the planned cuts include a planar tibial cut and multiple planar femoral cuts, for example as described above with reference to FIG. 1. The planned cuts can be defined relative to the virtual bone models used in the implant planning workflow at step 408. Based on registration processes from step 404 which define a relationship between tracked fiducial markers and the virtual bone models, the positions and orientations of the planned cuts can also be defined relative to the tracked fiducial markers, (e.g., in a coordinate system used by the tracking system 222). The surgical system 200 is thereby configured to associate the planned cuts output from step 408 with corresponding planes or other geometries in real space.

At step 410, a bone preparation workflow is provided, for example, by the surgical system 200. The bone preparation workflow includes guiding execution of one or more cuts or other bone modifications based on the surgical plan created at step 408. For example, as explained in detail above with reference to FIGS. 2-3, the bone preparation workflow may include providing haptic feedback which constrains the surgical tool 234 to a plane associated with a planned cut to facilitate use of the surgical tool 234 to make that planned cut. In other embodiments, the bone preparation workflow can include automatically controlling the robotic device 220 to autonomously make one or more cuts or other bone modifications to carry out the surgical plan created at step 408. In other embodiments, the bone preparation workflow comprises causing the robotic device 220 to hold a cutting guide, drill guide, jig, etc. in a substantially fixed position that allows a separate surgical tool to be used to execute the planned cut while being confined by the cutting guide, drill guide, jig, etc. The bone preparation workflow can thus include control of a robotic device in accordance with the surgical plan.

The bone preparation workflow at step 410 can also include displaying graphical user interface elements configured to guide a surgeon in completing one or more planned cuts. For example, the bone preparation workflow can include tracking the position of a surgical tool relative to a plane or other geometry associated with a planned cut and relative to the bone to be cut. In this example, the bone preparation workflow can include displaying, in real-time, the relative positions of the surgical tool, cut plane or other geometry, and bone model. In some embodiments, visual, audio, or haptic warnings can be provided to indicate completion or start of an event or step of the procedure, entry or exit from a state or virtual object, interruptions to performance of the planned cut, deviation from the planned cut, or violation of other criteria relating to the bone preparation workflow.

In some embodiments, step 410 is provided until all bone cuts planned at step 408 are complete and the bones are ready to be coupled to the implant components. In other embodiments, for example as shown in FIG. 4, a first iteration of step 410 can include performing only a portion of the planned cuts. For example, in a total knee arthroplasty procedure, a first iteration of step 410 can include making a tibial cut to provide a planar surface on the tibia without modifying the femur in the first iteration of step 410.

Following an iteration of the bone preparation workflow at step 410, the process 400 can proceed to step 412. At step 412 a mid-resection tensioning workflow or a trialing workflow is provided, for example by the surgical system 200. The mid-resection tensioning workflow is provided when less than all of the bone resection has been completed. The trialing workflow is provided when all resections have been made and/or bones are otherwise prepared to be temporarily coupled to trial implants. The mid-resection tensioning workflow and the trialing workflow at step 412 provide for collection of intraoperative data relating to relative positions of bones of the joint using the tracking system 222 including performing gap measurements or other tensioning procedures that can facilitate soft tissue balancing and/or adjustments to the surgical plan.

For example, step 412 may include displaying instructions to a user to move the joint through a range of motion, for example from flexion to extension, while the tracking system 222 tracks the bones. In some embodiments, gap distances between bones are determined from data collected by the tracking system 222 as a surgeon places the joint in both flexion and extension. In some embodiments, soft tissue tension or distraction forces are measured. Because one or more bone resections have been made before step 412 and soft tissue has been affected by the procedure, the mechanics of the joint may be different than during the initial assessment workflow of step 402 and relative to when the pre-operative imaging was performed. Accordingly, providing for intra-operative measurements in step 412 can provide information to a surgeon and to the surgical system 200 that was not available pre-operatively and which can be used to help fine tune the surgical plan.

From step 412, the process 400 returns to step 408 to provide the implant planning workflow again, now augmented with data collected during a mid-resection or trialing workflow at step 412. For example, planned gaps between implants can be calculated based on the intraoperative measurements collected at step 412, the planned position of a tibial implant relative to a tibia, and the planned position of a femoral implant relative to a femur. The planned gap values can then be displayed in an implant planning interface during step 408 to allow a surgeon to adjust the planned implant positions based on the calculated gap values. In various embodiments, a second iteration of step 408 to provide the implant planning workflow incorporates various data from step 412 in order to facilitate a surgeon in modifying and fine-tuning the surgical plan intraoperatively.

Steps 408, 410, and 412 can be performed multiple times to provide for intra-operative updates to the surgical plan based on intraoperative measurements collected between bone resections. For example, in some cases, a first iteration of steps 408, 410, and 412 includes planning a tibial cut in step 408, executing the planned tibial cut in step 410, and providing a mid-resection tensioning workflow in step 414. In this example, a second iteration of steps 408, 410, and 412 can include planning femoral cuts using data collected in the mid-resection tensioning workflow in step 408, executing the femoral cuts in step 410, and providing a trialing workflow in step 412. Providing the trialing workflow can include displaying instructions relating to placing trial implants on the prepared bone surfaces, and, in some embodiments, verifying that the trial implants are positioned in planned positions using the tracking system 222. Tracking data can be collected in a trialing workflow in step 412 relating to whether the trial implants are placed in acceptable positions or whether further adjustments to the surgical plan are needed by cycling back to step 408 and making further bone modifications in another iteration of step 410.

In some embodiments, executing process 400 can include providing users with options to jump between steps of the process 400 to enter a desired workflow. For example, a user can be allowed to switch between implant planning and bone preparation on demand. In other embodiments, executing process 400 can include ensuring that a particular sequence of steps of process 400 are followed. In various embodiments, any number of iterations of the various steps can be performed until a surgeon is satisfied that the bones have been properly prepared to receive implant components in clinically-appropriate positions.

As shown in FIG. 4, the process 400 includes step 414 where implantation of prosthetic components is facilitated. Once the bones have been prepared via step 410, the prosthetic components can be implanted. In some embodiments, step 414 is executed by the surgical system 200 by removing the robotic arm 232 from the surgical field and otherwise getting out of the way to allow a surgeon to fix the prosthetic components onto the bones without further assistance from the surgical system 200. In some embodiments, step 414 includes displaying instructions and/or navigational information that supports a surgeon in placing prosthetic components in the planned positions. In yet other embodiments, step 414 includes controlling the robotic arm 232 to place one or more prosthetic components in planned positions (e.g., holding a prosthetic component in the planned position while cement cures, while screws are inserted, constraining an impaction device to a planned trajectory). Process 400 can thereby result in prosthetic components being affixed to modified bones according to an intraoperatively updated surgical plan.

Figure 5:
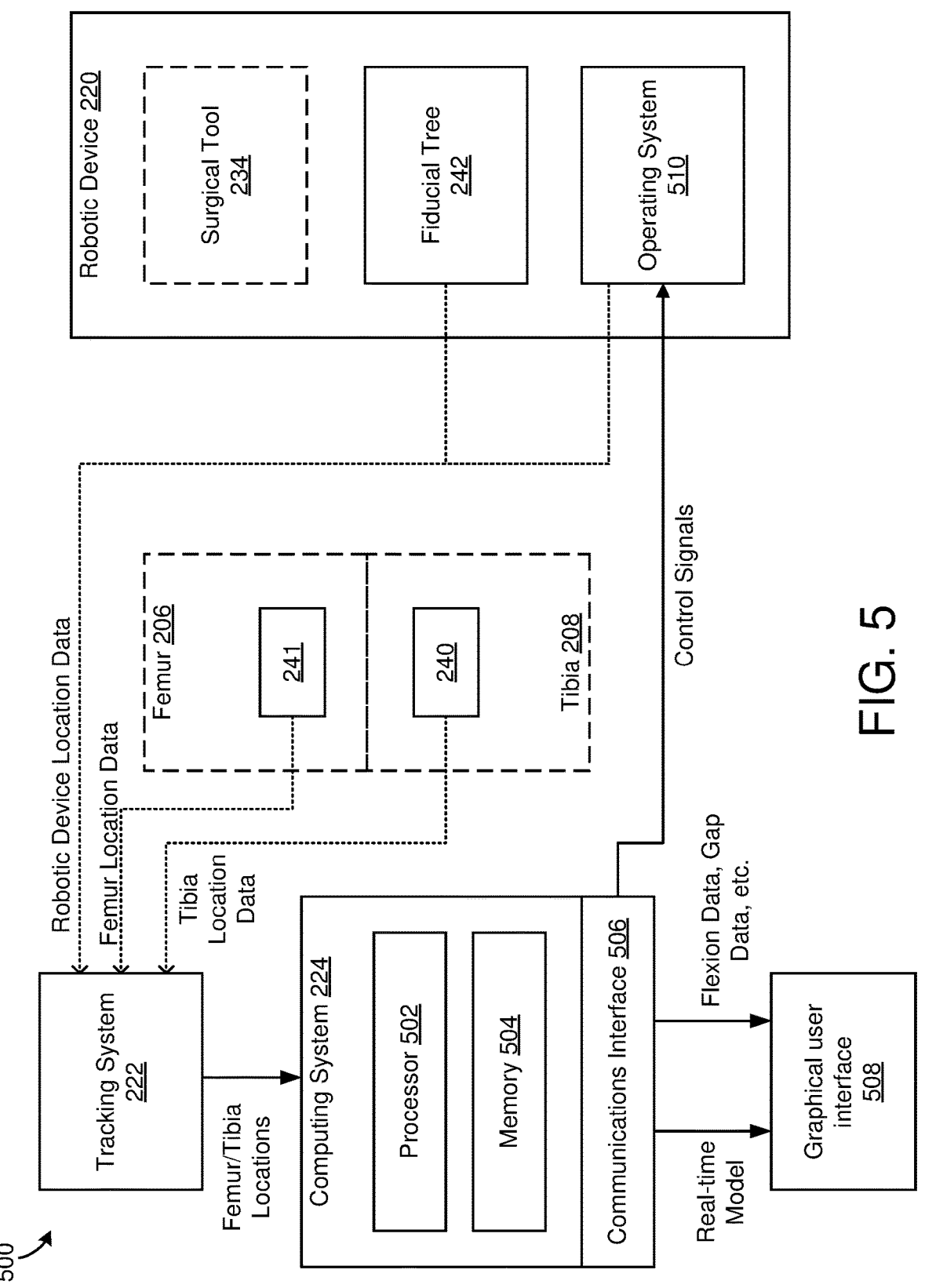
FIG. 5 is a block diagram of a surgical system, according to an exemplary embodiment.

Referring now to FIG. 5, a block diagram of a surgical system 500 for orthopedic surgery is shown, according to an exemplary embodiment. The surgical system 500 may be substantially similar to the surgical system 200, as described above. In some embodiments, surgical system 500 is another embodiment of surgical system 200. The surgical system 500 may include a robotic device 220, tracking system 222, computing system 224, a processor 502, a memory device 504, a communications interface 506, and/or a graphical user interface 508.

In some embodiments, the surgical system 500 is configured to provide the computing system 224 with the necessary information for determining an accurate and/or real-time position of the femur 206 and/or the tibia 208. The data may be provided to the computing system 224 via the tracking system 222, any of the fiducial trees 240-242, or any combination thereof. In some embodiments, the tracking system 222 obtains location data relating to the robotic device 220 by optically tracking the fiducial tree 242, which is coupled to the robotic device 220, and based on data from joint encoders of the robotic device 220. The tracking system 222 may further obtain tibia pose data (e.g., location and orientation data) using the fiducial tree 240, and femur pose data using the fiducial tree 241, as described above. The tracking system 222 and computing system 224 may thus be configured to determine the one or more locations and orientations of the bones (e.g., the femur 206 and the tibia 208). In other embodiments, the tracking system 222 and computing system 224 may also be configured to determine pose data (e.g., data of one or more locations and orientations) of implants, resections of a bone, ligaments, tissues, and/or any suitable anatomical object or tool.

For sake of example, the computing system 224 can use the tracked poses of the femur 206 and the tibia 208 to determine the relative positions of the femur 206 and the tibia 208. More specifically, the relative positions of a distal end of the femur 206 and a proximal end of the tibia 208. Using data from the tracking system 222, the computing system 224 can determine a medial gap between the femur 206 and the tibia 208 (e.g., the distance between the tibia 208 and a medial femoral condyle of the femur 206) (e.g., in millimeters) and a lateral gap between the femur 206 and the tibia 208 (e.g., the distance between the tibia 208 and a lateral femoral condyle of the femur 206) at a given point in time. The computing system 224 may use three-dimensional models (e.g., virtual bone models) of the femur 206 and the tibia 208 as part of calculating gap distances based on the tracking data. In some embodiments, the computing system 224 uses planned positions of bone and/or implant components relative to the virtual bone model of the femur 206 and tibia 208 as part of calculating gap distances. In such embodiments, the lateral and medial gaps may be calculated as planned gaps between points on the surfaces of the femur 206, the tibia 208, a femoral implant, a tibial implant, and/or any other suitable anatomical component. The computing system 224 may further be configured to display a virtual bone model and the gap measurements on the graphical user interface 508, update a visualization using the gap data, facilitate surgical planning using the gap data, and enable other processes described in greater detail below.

In other embodiments, the tracking system 222 may track poses of various other structures, for example implants (e.g., a tibial implant, a femoral implant, etc.), a point on a bone resection, a predefined anatomical point (e.g., a ligament insertion), and/or any other suitable anatomical object and/or location. Based on the data from the tracking system 222, the computing system 224 may determine various measurements (e.g., gap measurements, force measurements, distances, flexion angles, extension angles, etc.) between two bones, two implants, a bone and an implant, two predefined points, two bone resection cuts, an implant and a bone resection cut, and/or any other combination of suitable anatomical objects and/or locations. As discussed above, the computing system 224 may use a virtual bone model, planned positions of various anatomical structures, and/or other suitable surgical plan information as part of determining the various measurements. Although the examples discussed below refer to measurements (e.g., gap measurements, force measurements, flexion angles, extension angles, etc.) as they relate to a medial gap and a lateral gap between bones, these are for exemplary purposes only, and are not intended to be limiting.

The computing system 224 may also use the tracking data from the tracking system 222 to determine an angle between the femur 206 and the tibia 208, for example a flexion angle of the knee (e.g., an amount of bending of the knee through a range of motion of the knee). The flexion angle may be zero degrees when the knee is extended straight (i.e., with the femur 206 and tibia 208 parallel, and the posterior capsule tight) and may increase with bending of the knee. A flexion angle of 90 degrees indicates that the knee is bent at a right angle. Based on the data from the tracking system 222 indicating the relative poses of the femur 206 and the tibia 208, the computing system 224 can determine the flexion angle of the joint for a given point in time.

In some embodiments, the computing system 224 is communicably connected to the robotic device 220 (e.g., via operating system 510, etc.) and is configured to provide control signals to the robotic device 220, for example to provide for operation and/or movement of the surgical tool 234 based in part on the gap measurements. For example, the computing system 224 may obtain planned bone resections based in part on the gap measurements, and then control the robotic device 220 to guide the surgical tool 234 as the surgical tool 234 executes the planned bone resections. While gap measurements are discussed herein as the data used to alter or adjust the surgical procedure and/or planning, other data relating to the femur 206 and the tibia 208, such as ligament tension or ligament location may also be used.

Referring now to FIG. 6, a flowchart of a process 600 for capturing gap data (e.g., joint laxity data) based on an acceptable flexion angle is shown, according to an exemplary embodiment. The process 600 can be executed by the surgical system 500 of FIG. 5, for example. The process 600 can be implemented as part of the initial assessment workflow step 406 of FIG. 4, and/or the mid-resection tensioning workflow or trialing workflow step 412 of FIG. 4.

At step 602, a range of acceptable flexion angles is determined. The computing system 224 of the surgical system 500 may be configured to determine the range of acceptable flexion angles. In an exemplary embodiment, the range of acceptable flexion angels is unique to a patient. For example, the tracking system 222 and the computing system 224 may collect data (e.g., flexion angle data, medial ligament data, lateral ligament data, etc.) of the patient's knee first at full extension, and then gradually collect data as the surgical system 500 guides the patient's knee (e.g., via the surgeon) through various flexion angels. Based on the data collected (e.g., the flexion data at full extension, medial ligament tension, lateral ligament tension, etc.), the computing system 224 may calculate the range of acceptable flexion angles of the patient. In other embodiments, the range of acceptable flexion angles may be predetermined (e.g., as a result of system requirements, FDA requirements, or other regulatory requirements), set by user-selectable surgeon preferences, or calculated dynamically based on other measurements and anatomical data (e.g., data collected during the initial assessment workflow step 406 of FIG. 4). In an exemplary embodiment, the range of acceptable flexion angles may be between +5 degrees flexion to +20 degrees flexion relative to the flexion angle captured at full extension (i.e., such that the range of acceptable flexion angles is a function of a particular patient's flexion angle when at the full extension that can be reached by that patient's joint during an initial assessment). In some embodiments, the range of acceptable flexion angles may be displayed on a graphical user interface (e.g., graphical user interface 508).

At step 604, tracking data indicative of the relative poses of the bones is obtained. As discussed above, the tracking system 222 may obtain location data relating to the robotic device 220, the femur 206, and/or the tibia 208 using fiducial trees 240-242. In other embodiments, location data may be obtained for points on an implant, predefined anatomical points, a point on a cut, and/or any other suitable anatomical locations, as discussed above. For the sake of example, relative pose data (and subsequent gap and/or other measurements, discussed below) may be obtained based on the femur 206 and the tibia 208, and may be used as a primary example in subsequent examples. For example, the tracking system 222 may obtain tibia pose data (e.g., location and orientation data) using the fiducial tree 240, and femur pose data using the fiducial tree 241. This pose data may be relayed to the computing system 224, and the one or more locations and orientations of the femur 206 and the tibia 208 may be determined and stored. In some embodiments, the graphical user interface 508 may provide a virtual bone model that represents the one or more locations and orientations of the femur 206 and the tibia 208.

At step 606, the computing system 224 determines the current flexion angle of a joint. For example, once computing system 224 receives tracking data relating to the position and orientation of the femur 206 and the tibia 208, the computing system 224 may determine the current flexion angle of the bones (e.g., the tibia 208 relative to the femur 206). The graphical user interface 508 may provide a virtual bone model that displays the current flexion angle of the femur 206 and the tibia 208, provide a visual representation of the current flexion angle, and/or provide a numerical value for the current flexion angle. In some embodiments, the virtual bone model and the current flexion angle may be updated in real-time.

At step 608, the current flexion angle is displayed relative to the range of acceptable flexion angles. For example, the graphical user interface 508 may provide a visual representation of the current flexion angle, and a visual representation of the acceptable range of flexion angles. In some embodiments, the graphical user interface 508 may display a static flexion line (number line, axis, one-dimensional graph, etc.) upon which an indicator of the current flexion angle is displayed. An indicator of the acceptable range of flexion angles can also be included along the static flexion line. The static flexion line may provide a visual representation of flexion angles that span a variety of possible ranges, for example to full extension (e.g., zero degrees, a few degrees of extension/negative flexion) or a maximum flexion angle, which may be limited by a warning indicator (e.g., an arrow, a light, a button, a sound etc.). In other embodiments, the current flexion angle and/or the acceptable range of flexion angles may be displayed in a numerical table, chart, graph, or any other suitable visual display.

At step 610, a determination is made as to whether the current flexion angle is inside the range of acceptable flexion angles. For example, the computing system 224 may determine the current flexion angle of the femur 206 and the tibia 208, and determine whether the current flexion angle is inside the range of acceptable flexion angles obtained in step 602. In an exemplary embodiment, if the computing system 224 determines that the current flexion angle is within the acceptable range of flexion angles, the computing system 224 (via the graphical user interface 508) may provide an indication of such (e.g., change colors of the indicator of the current flexion angle, the representation of the range of acceptable flexion angles, the current flexion angle number, a button on the graphical user interface, etc.). Moreover, if the computing system 224 determines that the current flexion angle is within the acceptable range of flexion angles, the computing system 224 may proceed to step 612 and allow capture of gap data (e.g., the lateral gap, the medial gap, both gaps, delta gap data, etc.) to be stored in computing system 224. In some embodiments, relative poses of the femur 206 and/or the tibia 208 may be collected by the surgical system 500 (e.g., the tracking system 222 and the computing system 224), and the relative pose data may be used to determine (e.g., via the computing system 224) the captured gap data (e.g., the lateral gap, the medial gap, both gaps, etc.)(e.g., distances between features such as lateral condyles, medial condyles, etc. of bones, implants, planned implants, resection surfaces, etc.). In other embodiments, the gap data may be automatically captured by surgical system 500 (e.g., computing system 224), captured in response to some user input (e.g., pressing a foot pedal, pressing a button on the surgical system 500, pressing a button on graphical user interface 508, via voice command, etc.), and/or calculated using another suitable means. In yet other embodiments, the relative pose data may be collected and used to determine other gap data (e.g., delta gap data, minimum gap data, etc.), as discussed below. Capturing the gap data can include storing the relative poses of the tracked bones when a maximum gap is achieved, and calculating a predicted or expected gap between implant components with the bones in that pose based on planned implant placements.

Also at step 610, if the computing system 224 determines that the current flexion angle is not within the acceptable range of flexion angles, the computing system 224 may proceed to step 614, and prevent capturing the gap data. In some embodiments, the graphical user interface 508 may display the virtual bone model, and update the current flexion angle and acceptable range of flexion angles in real-time. In other embodiments, the graphical user interface 508 may direct a user to manipulate the femur 206 and/or tibia 208 so as to position the joint within the acceptable range of flexion angles. Process 600 thereby ensures that gap measurements are collected with the joint in the desired range of flexion angles, improving accuracy and reliability of use of such data in planning and bone preparation steps of process 400.

Following steps 610, 612 and/or 614, the surgical system 500, tracking system 222, and computing system 224 may be used to repeat steps 606-610 of FIG. 6. The computing system 224 may be updated in real-time, such that the computing system 224 may repeatedly collect, store, and update the gap data (e.g., the lateral gap, the medial gap, both gaps, etc.), such that a maximum gap between the femur 206 and the tibia 208 may be determined and stored, as described below. In some embodiments, the gap data (e.g., the lateral gap, the medial gap, both gaps, etc.) may be collected and used in combination with predetermined requirements (e.g., pre-defined surgical system preferences), user-selectable data, other patient-specific anatomical data, etc. to compute gap data. The real-time gap data may be displayed on the graphical user interface 508 (e.g., in numerical form, as a line, in color, etc.), and may be stored in computing system 224.

Figure 7:
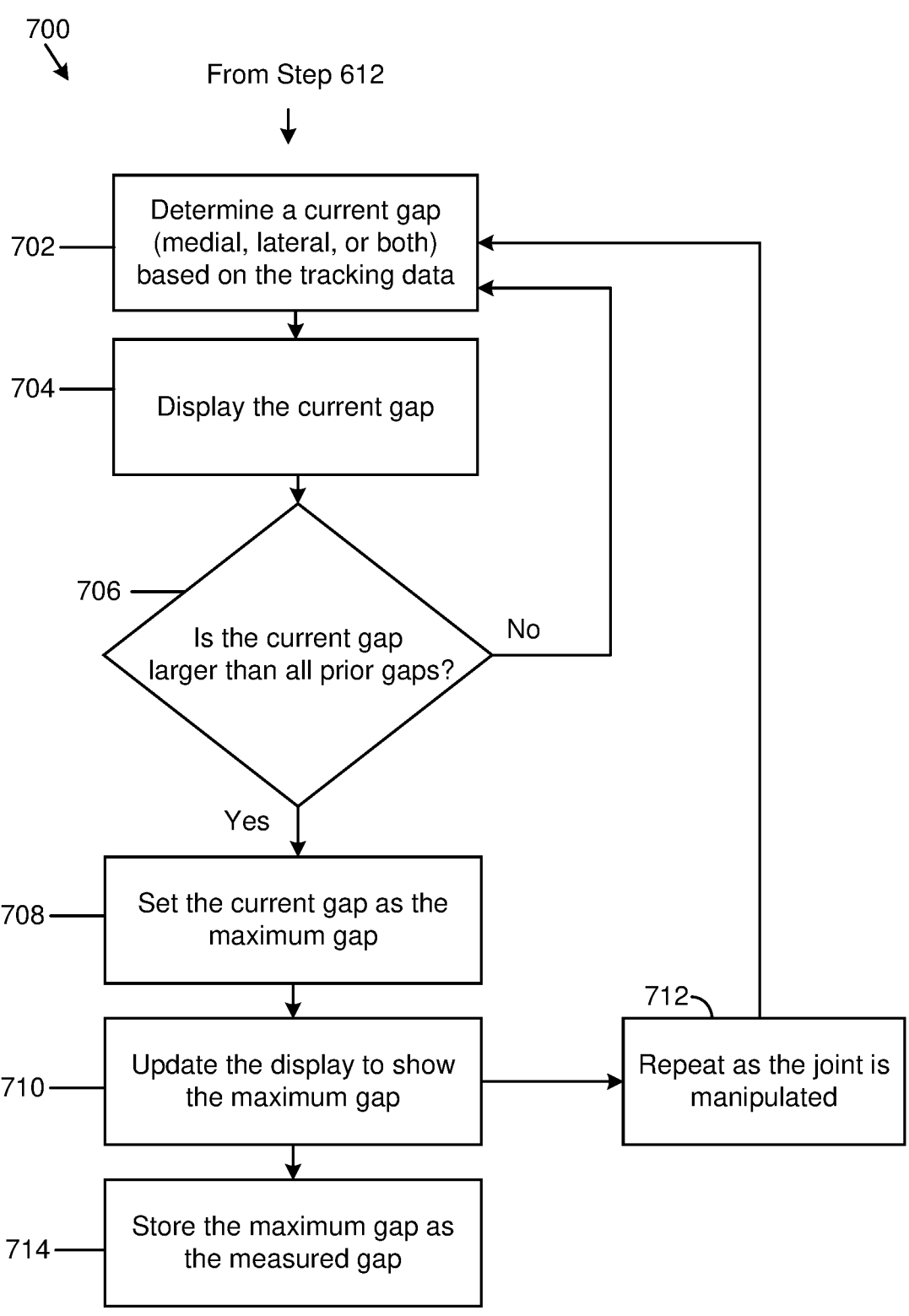
FIG. 7 is a flowchart of a second process that can be executed by the surgical system of FIG. 5, according to an exemplary embodiment.

Referring now to FIG. 7, a flowchart of a process 700 for capturing maximum gap measurements is shown, according to an exemplary embodiment. Following step 612 of FIG. 6, the process 700 may be used to capture maximum gap measurements, for example the maximum gap measurements of both the lateral and medial gaps, while the joint is both in extension and flexion. It should also be understood that, in other embodiments, the various steps described in process 700 of FIG. 7 may also be implemented following step 604 of FIG. 6, and may be used to collect (real-time) gap measurement data of both the lateral and medial gaps. The process of 700 can be executed by the surgical system 500 of FIG. 5, for example. The process 700 can also be implemented as part of the initial assessment workflow step 406 of FIG. 4, and/or the mid-resection tensioning workflow or trialing workflow step 412 of FIG. 4.

At step 702, the surgical system 500 determines a current gap measurement. For example, the tracking system 222 may obtain location and pose data relating to the femur 206 and the tibia 208 using fiducial trees 240-241. As discussed above, using data from the tracking system 222, the computing system 224 may determine the medial and/or lateral gaps between the femur 206 and the tibia 208. In an exemplary embodiment, the computing system 224 may determine the medial and/or lateral gaps using the data from the tracking system 222 (e.g., step 604 of FIG. 6) and pre-planned data (e.g., data from the implant planning workflow step 408 of FIG. 4, the bone preparation workflow step 410 of FIG. 4, or other suitable surgical plan data). In other embodiments, three-dimensional models of the femur 206 and the tibia 208 may be used with the tracking data to calculate the current gap(s). The computing system 224 may determine the medial and lateral gaps independently, or simultaneously, and may use virtual bone models of the femur 206 and the tibia 208 as part of calculating the gap measurements.

Figure 8:
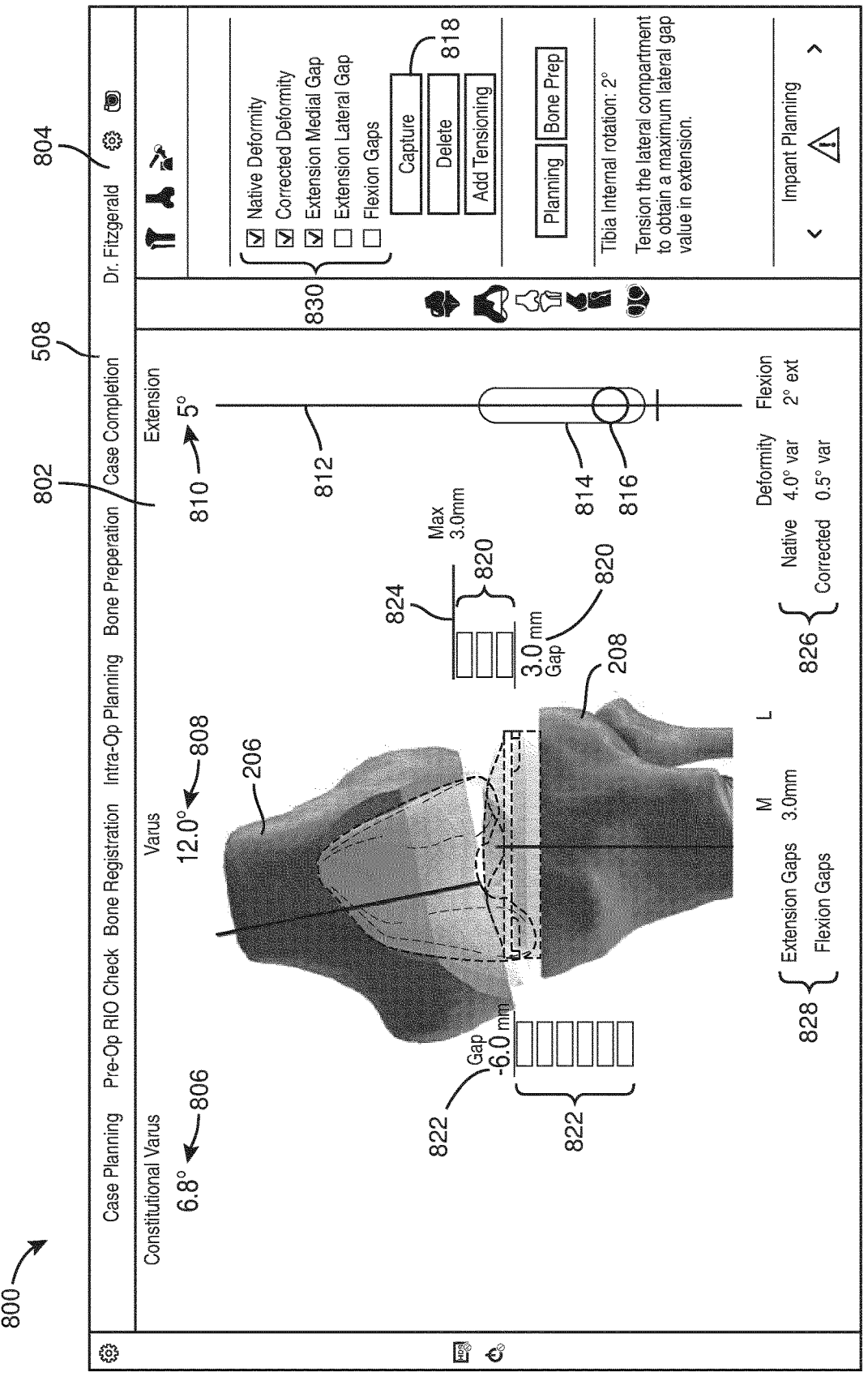
FIG. 8 is an illustration depicting an example implementation of the processes of FIG. 6 and FIG. 7, according to an exemplary embodiment.
Figure 9:
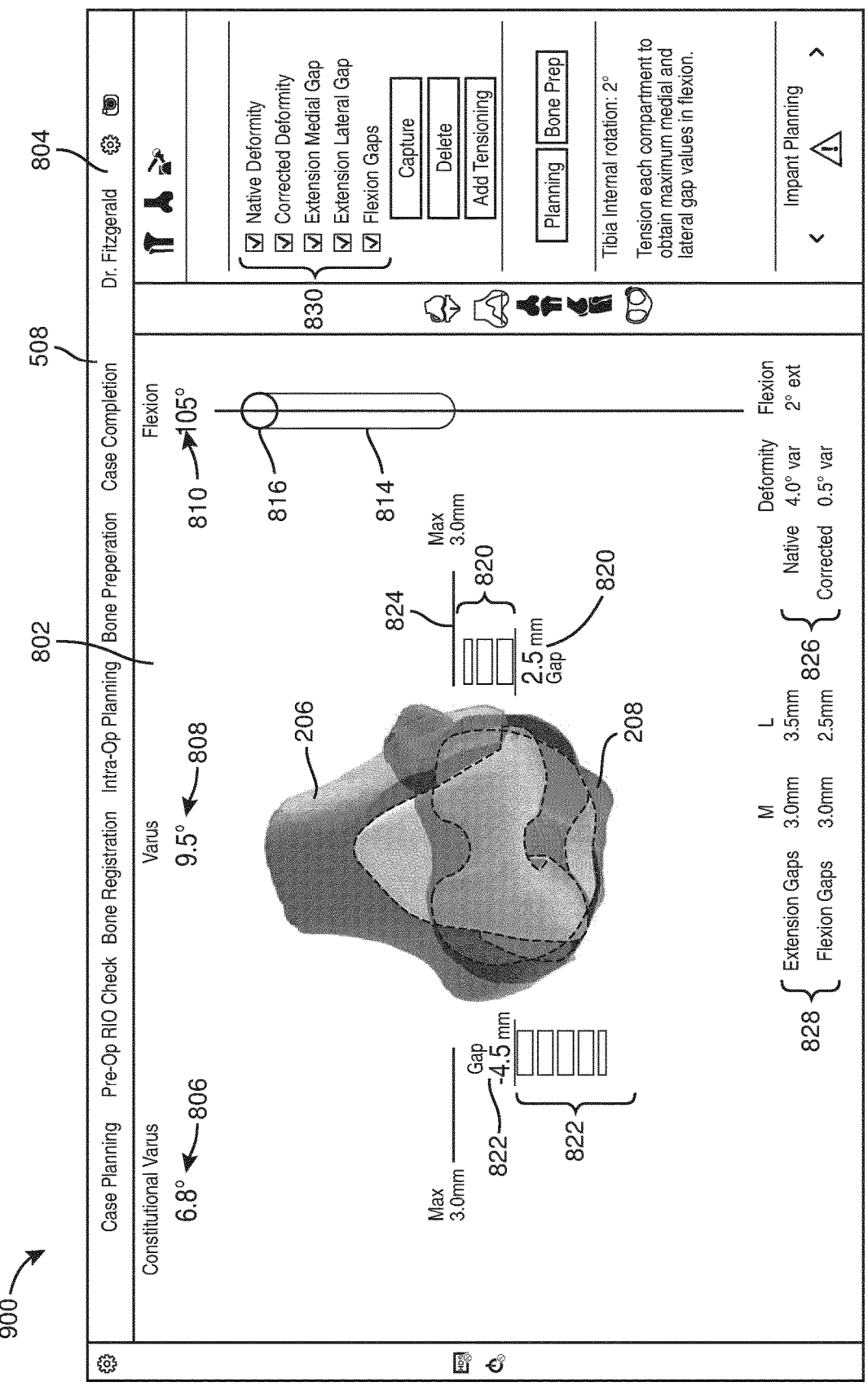
FIG. 9 is another illustration depicting an example implementation of the processes of FIG. 6 and FIG. 7, according to an exemplary embodiment.
Figure 10:
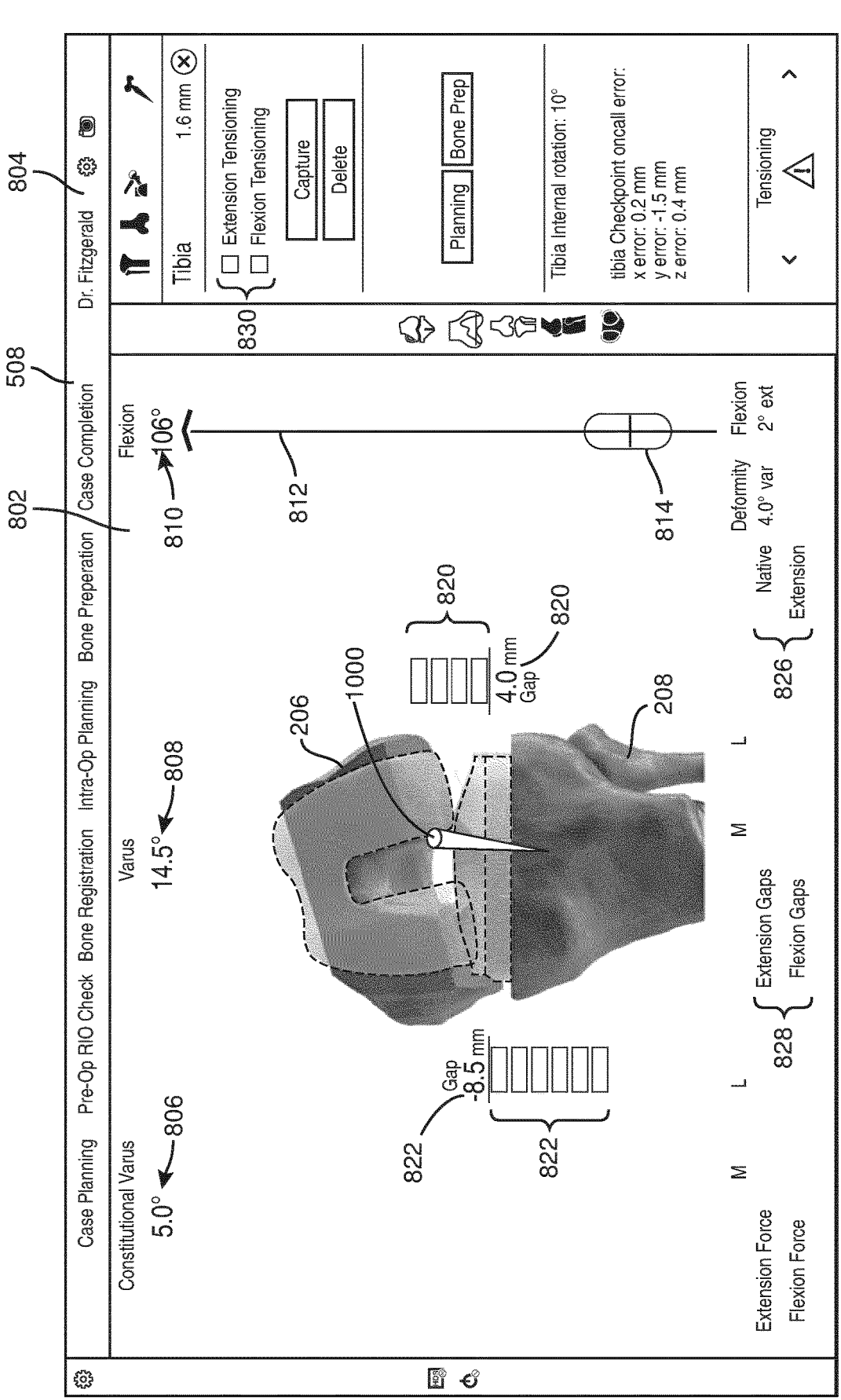
FIG. 10 is yet another illustration depicting an example implementation of the processes of FIG. 6 and FIG. 7, according to an exemplary embodiment.

At step 704, the surgical system 500 displays the current gap measurement. For example, the graphical user interface 508 may display the current gap measurement for the medial gap, the lateral gap, and/or both the medial and lateral gaps. The gap measurement may reflect a distance between two bones, a distance between two implant components (e.g., planned implants based on planned implant placement relative to the bones, trial implants, primary implants), a distance relative to a planned resection, etc. The graphical user interface 508 may display the current gap measurements in any suitable form (e.g., as ratcheting columns or stacks as shown in FIGS. 8-10, in numerical form, as a line, in color, etc.). In some embodiments, the graphical user interface 508 may provide a virtual bone model of the femur 206 and the tibia 208, which may include the gap measurements, and can be updated in real-time. In some embodiments, if the current gap measurement is larger than a threshold gap measurement (e.g., based on system requirements, FDA requirements, regulatory requirements, user-selectable preferences, calculated based on patient anatomical data, etc.), the surgical system 500 may provide a warning and/or modify the current gap.

At step 706, a determination is made as to whether the current gap measurement is larger than prior gap measurements. For example, the computing system 224 may determine a current gap measurement, and determine whether the current gap measurement is larger than the respective prior gap measurements (e.g., respective to the medial gap, lateral gap, while being extended, while being flexed, etc.). The prior gap measurements of each of the respective gaps (e.g., a prior maximum value for each gap) may be stored and referenced using computing system 224, memory device 504, or any other suitable storage device. If the current gap measurement is larger than all prior gap measurements for that respective gap (e.g., by comparing to a previously-stored maximum gap), the computing system 224 may proceed to step 708, permit capture, and set the current gap measurement as the maximum gap measurement (e.g., override the prior maximum gap measurement or the preset measurement). In some embodiments, the computing system 224 may determine the current gap measurement, and determine whether the current gap measurement is larger than the maximum gap measurement for that respective gap, as discussed below (e.g., computing system 224 may only compare the current gap measurement to the maximum gap measurement). In other embodiments, the computing system 224 may determine whether the current gap measurement is larger than gap measurements over a predetermined period of time for that respective gap (e.g., one minute, five minutes, etc.). In yet other embodiments, the current gap data may be collected and used to determine other gap data calculations (e.g., delta gap data, minimum gap data, etc.), as discussed below.

Also at step 706, if the computing system 224 determines that the current gap measurement is not larger than all respective prior gap measurements, the computing system 224 may return to step 702 (e.g., determine the current gap measurement). The determination by computing system 224 in step 706 may be completed for the medial gap, the lateral gap, and/or both the medial and lateral gap measurements, either independently or concurrently. Similarly, in some embodiments, if the computing system determines that the current gap measurement is not larger than the maximum gap measurement for that respective gap, the computing system may return to step 702.

At step 708, as discussed above, if the computing system 224 determines that the current gap measurement is larger than all respective prior gap measurements, the current gap measurement may be captured and set as the maximum gap measurement. The gap data may be automatically captured by surgical system 500 (e.g., computing system 224), for example at a high frequency (e.g., substantially real-time, multiple times per second), captured in response to user input (e.g., pressing a foot pedal, pressing a button in the surgical system 500, pressing a button on graphical user interface 508, via voice command, etc.), or captured in response to some other input. In some embodiments, as discussed above, if the computing system 224 determines that the current gap measurement is larger than the maximum gap measurement for that respective gap (e.g., based on prior gap measurements and/or the memory device 504), the current gap measurement may be captured and set as the maximum gap measurement. The maximum gap measurement may be updated and stored in computing system 224, memory device 504, or any other suitable storage device. Like other gap measurements, the maximum gap measurement may be displayed on the graphical user interface 508 (e.g., as ratcheting columns or stacks, in numerical form, as a line, in color, etc.).

At step 710, the computing system 224 may update the maximum gap measurement. For example, the graphical user interface 508 may provide a virtual bone model, which may include the gap measurements. The graphical user interface 508 may be updated in real time, and may be updated to show the maximum gap measurement in a variety of ways (e.g., in numerical form, as a line, in color, etc.).

Following step 710, a determination is made as to whether to collect the gap measurement in step 708 as the maximum gap measurement, or to repeat the steps of process 700 as the bones are manipulated. In step 712, the steps of process 700 may be repeated (e.g., determine a current gap, determine whether the current gap is larger than all prior gap measurements (and/or the maximum gap measurement), set as the maximum, etc.) as the femur 206, the tibia 208, and/or the joint are manipulated. The femur 206, tibia 208, and/or the joint may be manipulated by a surgeon, the surgical system 500 (e.g., the robotic device 220), or any other suitable device or procedure (e.g., tensioning device, motorized leg holder, etc.). As the femur 206, tibia 208, and/or joint are manipulated, the computing system 224 may determine the current gap measurement, and update the maximum gap measurement as described in process 700 above.

At step 714, the maximum gap measurement is collected and stored. For example, after the steps of process 700 described above have been completed, either once or after several iterations, the computing system 224 may store the maximum gap measurement. For example, process 700 may continue to execute iterations of the loop shown in FIG. 7 until a user provides an indication (e.g., selects a button, provides an input, pushes a pedal, etc.) that the maximum gap displayed should be stored as the measured gap (e.g., the maximum gap measurement). The maximum gap measurement may be stored in the computing system 224, memory device 504, or any other suitable storage device, and displayed on the graphical user interface 508 as the measured gap. As mentioned above, this process can be executed to store the medial gap, the lateral gap, or both gaps simultaneously in various embodiments and under different settings of the computing system 224.

Referring now to FIG. 8, an illustration of a possible implementation of the processes of FIG. 6 and FIG. 7 is shown, according to an exemplary embodiment. The illustration shows a coronal view of a virtual bone model in the graphical user interface 508, which may be provided via the display 264 of the surgical system 200 (e.g., surgical system 500) during the initial assessment workflow step 406 of FIG. 4. The graphical user interface 508 may be updated in real-time, to display a real-time virtual bone model of the femur 206 and the tibia 208, or other information and measurements of processes 600 of FIGS. 6 and 700 of FIG. 7. The graphical user interface 508 may also display the information from processes 600 and 700 in model window 802, and/or tab bar 804.

The model window 802 provides a user with information regarding processes 600 and 700. For example, the model window 802 displays a real-time virtual bone model of the femur 206 and the tibia 208, showing the real-time tracked poses of the femur 206 and the tibia 208. The model window 802 may also display other pose and orientation information relating to the femur 206 and the tibia 208, obtained from the tracking system 222 and/or the computing system 224 (e.g., steps 604-606, etc.), for example a constitutional varus angle 806, a varus angle 808, and a flexion angle 810. In some embodiments, the constitutional varus angle 806 and the varus angle 808 are instead displayed as valgus angles. The flexion angle 810 indicates the current flexion angle of the tibia 208 relative to the femur 206.

The model window 802 is also shown to include a static flexion line 812 with a pill box 814 and an indicator 816 associated with a flexion angle 810. The indicator 816 indicates a current flexion angle, while the pill box 814 indicates a range of acceptable flexion angles for a given step of the workflow. The static flexion line 812 provides a visual representation of the location of the pill box 814 and the indicator 816, relative to a flexion angle 810, and may also include an indication of full extension (e.g., zero degrees) and/or a maximum flexion angle. As discussed above with regard to process 600 of FIG. 6 (e.g., step 602), the surgical system 500 (e.g., computing system 224) may determine a range of acceptable flexion angles. This range of acceptable flexion angles may be stored in computing system 224, and represented and displayed on the graphical user interface 508 in the form of the pill box 814. The range of acceptable flexion angles may be different based on predetermined requirements (e.g., FDA requirements, pre-defined based on the surgical system, etc.), user-selectable preferences, and/or other patient-specific anatomical data (e.g., full extension data, flexion angle data, medial ligament data, lateral ligament data, etc.) As such, pill box 814 may be different sizes, and displayed at different locations along static flexion line 812.

Similarly, as discussed above in regard to FIG. 6 (e.g., steps 604-606), the tracking system 222 and the computing system 224 may use real-time tracking data from the femur 206 and the tibia 208 to determine a current flexion angle of the knee. The computing system 224 may determine the current flexion angle, and relay that information to be represented and displayed on the graphical user interface 508 in the form of indicator 816. As the current flexion angle changes (e.g., via surgeon manipulation, patient repositioning, manipulation with a robotic device or surgical device, etc.), the indicator 816 may be displayed at different locations along the static flexion line 812.

As shown in FIG. 8, the indicator 816 is inside the pill box 814. As described above with regard to FIG. 6 (e.g., steps 608-614), once the tracking system 222 and the computing system 224 determine and display (e.g., via graphical user interface 508) the range of acceptable flexion angles (e.g., via pill box 814), and the current flexion angle (e.g., via indicator 816), the computing system 224 may determine whether the current flexion angle is within the acceptable range of flexion angles. As discussed above with regard to FIG. 6 (e.g., step 610), if the computing system 224 determines that the current flexion angle (e.g., the indicator 816) is within the acceptable range of flexion angles (e.g., the pill box 814), the model window 802 may provide an indication of such (e.g., change colors of the pill box 814, the indicator 816, the flexion angle 810, the static flexion line 812, a button on the model window 802, etc.). As shown in FIG. 8, when the current flexion angle is inside the range of acceptable flexion angles, the computing system 224 may permit a capture button 818 to be pressed in order to capture gap measurement data (e.g., the lateral gap, the medial gap, and/or both gaps, while the joint is extended or flexed). As discussed above, the gap data may be automatically captured via the computing system 224, or captured in response to some other user input. In some embodiments, if the computing system 224 determines that the current flexion angle is not inside the range of acceptable flexion angles (e.g., the indicator 816 is not within the pill box 814, and/or the model window 802 has not changed the color of the pill box 814 and the indicator 816), the computing system 224 may prevent capture button 818 from being pressed, and prevent capturing the gap measurement data. In an exemplary embodiment, displaying the pill box 814 and the indicator 816 relative to one another, and along the static flexion line 812 allows a user to easily and intuitively see whether an acceptable flexion angle is achieved and, if not, how to manipulate the joint to move the current flexion angle into the range of acceptable flexion angles.

In addition to the information relating to process 600 of FIG. 6, the model window 802 provides information regarding process 700 of FIG. 7. For example, the model window 802 may display real-time gap measurements on the graphical user interface 508 as columns and/or stacks of varying sizes (e.g., gap measurements 820 and 822). The gap measurements may include: a lateral gap measurement 820 and a medial gap measurement 822, which may be displayed in the form of the ratcheting columns and/or in numerical form. In an exemplary embodiment, the real-time gap measurements may be determined using real-time pose tibia and femur data (e.g., step 604 of FIG. 6). In some embodiments, and as discussed above with regard to steps 610-612 of FIG. 6, once the tracking system 222 and the computing system 224 determine that the current flexion angle is inside the range of acceptable flexion angles (e.g. as shown in FIG. 8), the computing system 224 may capture lateral gap measurement 820, medial gap measurement 822, and/or both, either individually, or at the same time. The gap measurements can be displayed on the graphical user interface 508, and stored in computing system 224, memory device 504, or any other suitable storage device.

The tracking system 222 and the computing system 224 may update the graphical user interface 508 in real-time, such that the model window 802 may display the lateral gap measurement 820 and the medial gap measurement 822 in real-time (e.g., the numbers and ratcheting columns of gap measurements 820 and/or 822 may fluctuate in real-time). As discussed above with regard to process 700 of FIG. 7, in an exemplary embodiment the tracking system 222 and the computing system 224 may determine current gap measurements, and determine whether the current gap measurements are larger than all prior respective gap measurements (e.g., medial, lateral, extended or flexed). If the current gap measurement is larger than all prior respective gap measurements, the computing system 224 may capture and set the current gap measurement as a maximum gap measurement (e.g., maximum gap measurement 824, shown as maximum gap measurement line 824). In some embodiments, as discussed above, the computing system may determine whether the current gap measurement is larger than the maximum gap measurement for that respective gap. The gap data may be set as the maximum gap measurement automatically, or in response to user input. In FIG. 8, the current lateral gap measurement 820 is shown as the maximum gap measurement 824 for the lateral gap in the extended position. As discussed above in FIG. 7, the real-time gap capture steps of process 700 can be repeated as the joint is manipulated, and the model window 802 may provide real-time measurements and information in response to such manipulation. Once it is determined that the maximum gap measurement 824 has been determined, the maximum gap measurement 824 may be displayed on graphical user interface 508 (e.g., in model window 802), and stored in the computing system 224, memory device 504, or any other suitable storage device, in some embodiments along with other data relating to the poses of tracked bones when the maximum gap was achieved.

The model window 802 may also provide information that may be helpful in process 400 of FIG. 4 (e.g., steps 408 or 412 of FIG. 4), and the processes of FIG. 6 and FIG. 7. For example, the model window 802 may include an angle measurement table 826. The angle measurement table 826 may contain information regarding the maximum joint flexion, the native deformity of the joint (e.g., varus or valgus, varus deformity at terminal extension, etc.), and/or information regarding the corrected deformity of a joint (e.g., after a surgeon provides thrust, assistance from a surgical device, a surgical procedure, or any other suitable manipulation). The information collected in angle measurement table 826 may be used to determine the overall alignment of the joint, and/or to determine the range of acceptable flexion angles, as discussed above. In addition, the model window 802 may include a gap measurement table 828. The gap measurement table 828 may contain maximum gap measurements for the medial and lateral gaps, both as the joint is extended and flexed. The maximum gap measurements may be updated in the gap measurement table 828 as processes 600 and 700 are repeated. In FIG. 8, the gap measurement table 828 includes a measurement for the medial extension gap (e.g., 3.0 mm), which corresponds to the maximum gap measurement 824 discussed above. In other embodiments, the gap measurement table 828 may represent the real-time gap measurements (e.g., current gap measurements), as discussed below. In some embodiments, the information collected in the angle measurement table 826 and/or the gap measurement table 828 may provide an interactive review functionality, as discussed below.

The tab bar 804 provides a user with an interface that displays processes in a surgical plan. For example, the tab bar 804 allows a user to move between the steps in process 400 of FIG. 4 (e.g., steps 406-412), the steps in process 600 of FIG. 6, and the steps in process 700 of FIG. 7. In some embodiments, the tab bar 804 may provide a checklist 830 of the measurements that are needed to provide an initial assessment workflow step 406 of FIG. 4. For example, checklist 830 may recommend capturing native deformity, corrected deformity, extension medial gap, extension lateral gap, and flexion gap data. As shown in checklist 830, and the gap measurement table 828, FIG. 8 shows the extension lateral gap measurement data collection phase (e.g. the maximum lateral gap is measured while the joint is extended). As the checklist 830 is completed, the information may be stored and updated in the angle measurement table 826 and the gap measurement table 828 (e.g., via computing system 224).

Referring now to FIG. 9, another illustration of a possible implementation of the processes of FIG. 6 and FIG. 7 is shown, according to an exemplary embodiment. Like FIG. 8, the illustration of FIG. 9 shows a view of a virtual bone model in the graphical user interface 508, which may be provided during the initial assessment workflow step 406 of FIG. 4. The graphical user interface 508 may be updated in real-time, to display a real-time virtual bone model of the femur 206 and the tibia 208, or other information and measurements of processes 600 and 700. The graphical user interface may also display the information from processes 600 and 700 in model window 802, or tab bar 804.

The model window 802 of FIG. 9 shows another (e.g., transverse) view of a virtual bone model of the femur 206 and the tibia 208. Like FIG. 8, the model window 802 displays pose and orientation information relating to the femur 206 and the tibia 208, obtained from the tracking system 222 and/or computing system 224 (e.g., steps 604-606, etc.), for example the constitutional varus angle 806, a varus angle 808, and a flexion angle 810. Similarly, the tracking system 222 and computing system 224 may determine and display the range of acceptable flexion angles (e.g., via the pill box 814), and the current flexion angle (e.g., via the indicator 816), as discussed above.

The tracking system 222 and the computing system 224 may update the graphical user interface 508 in real-time, such that the model window 802 may display the lateral gap measurement 820 and the medial gap measurement 822 in real-time. As shown FIG. 9, the graphical user interface 508 may show the current gap measurement (e.g., numbers and columns of gap measurements 820 and/or 822) relative to the maximum gap measurement 824 (e.g., solid line) and other maximum gap measurements. As process 700 is executed, the maximum gap measurement line 824 may "ratchet" upwards whenever a larger gap is achieved (i.e., steps 706-710). The interface of FIG. 9 can be used as processes 600 and 700 are repeated for all gap measurements (e.g., medial and lateral, while the joint is extended or flexed, etc.) and the gap measurement table 828 may be updated and displayed on the graphical user interface 508 (e.g., in model window 802). In FIG. 9, the model window 802 shows gap measurement table 828 complete, indicating that processes 600 and 700 have been completed for all the maximum gap measurements. These maximum gap measurements may be stored in the computing system 224, the memory device 504, or any other device suitable for storage.

Like FIG. 8, the tab bar 804 of FIG. 9 provides a user with an interface displaying processes in a surgical plan. The checklist 830 may provide a list of measurements that are needed to provide an initial assessment workflow step 406 of FIG. 4. As shown in the checklist 830, and the gap measurement table 828, FIG. 9 shows the flexion gap measurement data collection phase (e.g., the maximum lateral and the maximum medial gaps are measured while the joint is flexed). Once checklist 830 is complete, the angle measurement table 826 and the gap measurement table 828 may be populated, and the information in the tables 826 and 828 may be stored in computing system 224.

Referring now to FIG. 10, another illustration of a possible implementation of some processes of FIG. 6 and FIG. 7 is shown, according to an exemplary embodiment. Like FIG. 8 and FIG. 9, the illustration of FIG. 10 shows a virtual bone model in a graphical user interface 508, which may be updated in real-time, to display a real-time virtual bone model of the femur 206 and the tibia 208, or other measurements of processes 600 and 700. The illustration of FIG. 10 may be provided during the mid-resection tensioning workflow, or the trialing workflow, of step 412 of FIG. 4 (e.g., following a bone preparation workflow step 410 where one or more cuts, or other bone modifications may be executed). As discussed above, because FIG. 10 may be provided during the mid-resection tensioning workflow (or the trialing workflow) of step 412, the illustration of FIG. 10 may provide additional intraoperative information and/or measurements relating to the relative positions of the bones or joint to facilitate soft tissue balancing and/or adjustments to a surgical plan.

The model window 802 of FIG. 10 shows another view of the virtual bone model of the femur 206 and the tibia 208, with the joint in flexion. Like FIG. 8 and FIG. 9, the model window 802 of FIG. 10 displays pose and orientation information relating to the femur 206 and the tibia 208, obtained from the tracking system 222 and/or computing system 224 (e.g., constitutional varus angle 806, varus angle 808, flexion angle 810, etc.). Similarly, the model window 802 displays the lateral gap measurement 820 and the medial gap measurement 822 in real-time (e.g., numbers and live gap columns), as well as, the angle measurement table 826 and the gap measurement table 828.

The model window 802 of FIG. 10 may display the virtual bone model of the femur 206 and the tibia 208 after one or more cuts, or other modifications to the bones have been executed. As such, some of the processes 600 and 700 of FIG. 6 and FIG. 7 may be repeated to collect and record angle measurement data and gap measurement data, which may provide additional intraoperative information on the bones, soft tissues, and/or joints. The model window 802 shows gap measurement table 828 incomplete, indicating that some of processes 600 and 700 may need to be completed for all the gap measurements. For example, real-time gap measurement data (e.g., current gap measurement data) may be determined (e.g., process 600, and steps 702-704), collected, captured, and stored in the gap measurement table 828. In addition, the model window 802 displays a visualization of a live tracked probe 1000. The visualization of the live tracked probe 1000 may be used to collect measurements or other information relating to the mid-resection tensioning workflow step 412 (e.g., contact bones, contact checkpoints, paint or contact one or more surfaces of a bone, etc.), either alone or in combination with the processes of FIG. 6 and FIG. 7.

Like FIG. 8 and FIG. 9, the tab bar 804 of FIG. 10 provides a user with an interface displaying processes in a surgical plan. The checklist 830 may provide a list of measurements that are needed to provide a mid-resection tensioning workflow (or the trialing workflow) of step 412 of FIG. 4. As shown in the checklist 830, and the gap measurement table 828, FIG. 10 shows the extension tensioning data collection phase (e.g., the current medial and current lateral gaps are measured while the joint is extended). Once the checklist 830 is complete, and the angle measurement table 826 and the gap measurement table 828 are populated, the information in tables 826 and 828 may be stored in the computing system 224, the memory device 504, or any other device suitable for storage.

Figure 11:
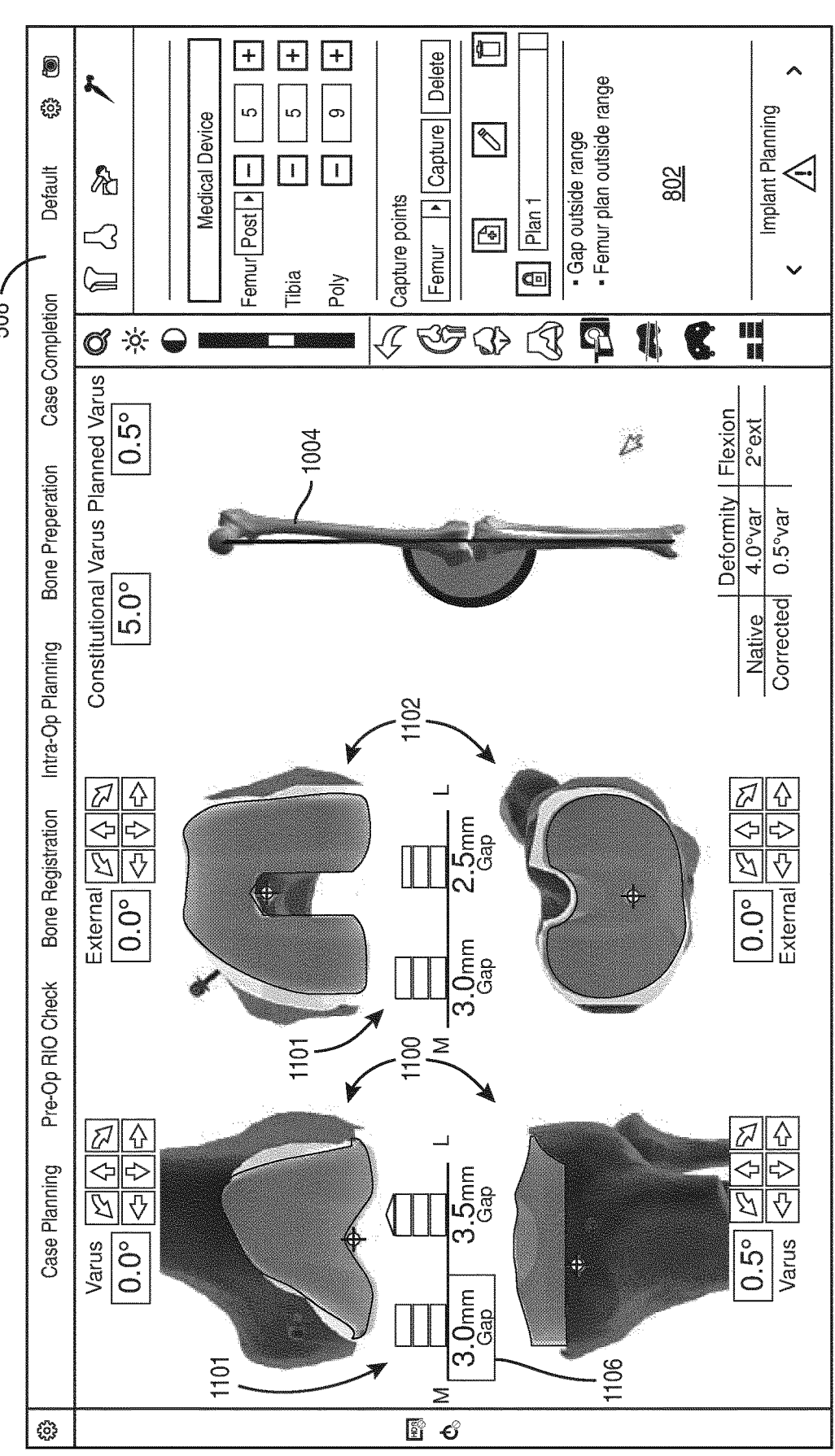
FIG. 11 is an illustration depicting an example implementation of the processes of FIG. 4, according to an exemplary embodiment.

Referring now to FIG. 11, an illustration of a possible implementation of some processes of FIG. 4 is shown, according to an exemplary embodiment. For example, following the gap measurement and data collection processes 600 and 700 of FIG. 6 and FIG. 7 (and FIGS. 8-9), as part of the initial assessment workflow step 406 of FIG. 4, the gap measurements and data may be used to provide an implant planning workflow step 408 and/or a bone preparation workflow step 410 of FIG. 4. The illustration of FIG. 11 shows several views of a virtual bone model in a graphical user interface 508, which may be updated based on data from processes 600 and 700.

The illustration in FIG. 11 shows several views of the knee joint, and corresponding gap data, in the implant planning workflow step 408 and/or the bone preparation workflow step 410 of FIG. 4. For example, knee extension view 1100, knee flexion view 1102, and long limb view 1104 may be shown, and corresponding gap measurement data may be shown in column and numerical form. The lateral gap measurements 820, and medial gap measurements 822, which may have been collected (e.g., captured poses) for both knee extension and flexion, may be shown below their corresponding views (e.g., gap measurement table 828 from FIG. 9 may be displayed in columns 1101 and numerical form below the corresponding views), or may be used to calculate gap distances predicted to result from the implant positioning and surgical plan being displayed and modified in the implant planning workflow via the interface of FIG. 11. That is, the columns 1101 may be updated as the user adjusts implant placement using the interface of FIG. 11 (e.g., by pressing arrows shown on the interface) in order to show the gap distances expected to be achieved in the patient's joint if implants are installed as planned. The interface of FIG. 11 may also display a warning indicator 1106, which may indicate that a gap measurement is outside an acceptable range (e.g., predetermined range, surgeon preference range, etc.). The gap measurement data displayed in the illustration of FIG. 11, and collected as described above, may thus be used to plan, modify, etc. a surgical plan (e.g., bone resections) in order to guide bone preparation and/or implant placement during a surgical procedure. For example, the data may be used to provide a bone preparation workflow step 410 of FIG. 4, provide a mid-resection tensioning workflow, or a trialing workflow, step 412 of FIG. 4 (e.g., steps illustrated in FIG. 10), or any combination thereof.

Figure 12:
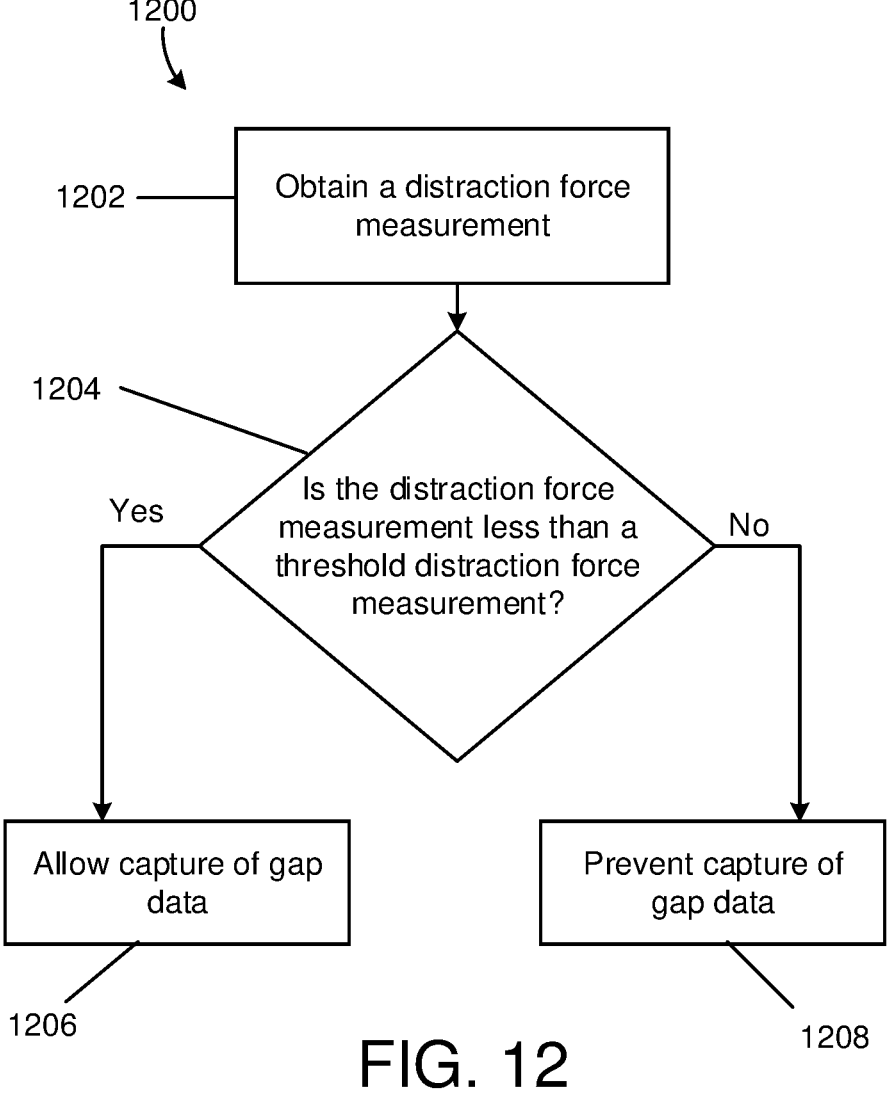
FIG. 12 is a flowchart of another process that can be executed by the surgical system of FIG. 5, according to an exemplary embodiment.

Referring now to FIG. 12, a flowchart of process 1200 for capturing gap data based on an acceptable distraction force is shown, according to an exemplary embodiment. The process 1200 may be executed by the surgical system 500 of FIG. 5, for example. The process 1200 may be executed as part of the initial assessment workflow step 406 of FIG. 4, in combination or independently of processes 600 and 700 of FIG. 6 and FIG. 7. In an exemplary embodiment, the process 1200 may also be implemented as part of the mid-resection tensioning workflow, or the trialing workflow, of step 412 of FIG. 4 (e.g., following a bone preparation workflow step 410 where one or more cuts, or other bone modifications may be executed). As discussed above with regard to FIG. 10, because process 1200 is provided during the mid-resection tensioning workflow (or trialing workflow), the process 1200 may provide additional intraoperative information and/or measurements relating to the relative positions of the bones or joint to facilitate soft tissue balancing and/or adjustments to the surgical plan.

Throughout process 1200, a distraction device may be used to distract (e.g., separate, force apart, etc.) the femur 206 and the tibia 208. The distraction device may be used to test ligament tension at various distraction distances. In some embodiments, the distraction device may be configured for manually sensing ligament tension (e.g., a surgeon feels the tension and force exerted), may include a force sensor configured to measure a distraction force, and/or may be configured to provide an indication of a distance of separation (e.g., distance between the distal ends of the working portion of the distraction device). The distraction device may be hand-held, configured for user manipulation. In other embodiments, the distraction devices is mounted on and operated by the robotic device 220. The distraction device may be configured to provide measurements of a distraction force (and, in some embodiments, distance measurements) to a surgical system (e.g., the surgical system 200, the surgical system 500) for use in computer-assisted surgical planning or to control a robotic device. For example, a warning can be generated if the distraction force on a medial and/or lateral side exceeds a preset value, or if the medial and lateral force differ by greater than a threshold amount.

The distraction device may be configured to interact with a tracking system (e.g., tracking system 222), and one or more distraction devices may be used individually or in combination (e.g., simultaneously) during various processes of a surgical plan. Using distraction devices with force sensors and/or distance measuring systems during a surgical procedure is described in U.S. application Ser. No. 17/004, 773, titled "Distraction Device with Disposable Force Sensor Pod," filed Aug. 27, 2020, and incorporated by reference herein in its entirety.

As discussed above, prior to process 1200, a distraction device may be positioned at the femur 206 and the tibia 208 as part of the mid-resection tensioning workflow, or the trialing workflow, of step 412 of FIG. 4. As part of step 412, a distraction device may be used, which may include a force sensor or a plurality of force sensors. The distraction device may be positioned at the knee, and the distraction device (e.g., force sensor) may measure the distraction force provided by the distraction device to the femur 206 and/or the tibia 208. In some embodiments, the distraction device may measure the distraction force provided to points on a bone (e.g., the medial condyle, the lateral condyle, etc.). In some embodiments, the distraction device may also measure the distance of separation between the distal ends of the distraction device, and may be configured to provide the force and distance measurements to a surgical system 500. In yet other embodiments, the distraction force data, the distraction distance data, and/or tracking data associated with the distraction device may be communicated to the surgical system 500 (e.g., the computing system 224) in real-time, and the distraction force and distance data, as well as, the location of the distraction device may be displayed relative to a virtual bone model via a graphical user interface.

At step 1202, the computing system 224 obtains a distraction force measurement. For example, once the distraction device (e.g., force sensor) measures a distraction force at the femur 206 and/or the tibia 208, and provides the force measurement to the surgical system (e.g., the surgical system 200, the surgical system 500, etc.), the computing system 224 may obtain a distraction force measurement. Similar to FIG. 6 and FIG. 7, the tracking system 222 may relay femur 206 and tibia 208 pose data (e.g., location and orientation data) to the computing system 224, and the graphical user interface 508 may provide a virtual bone model that represents the locations and orientations of the femur 206 and the tibia 208, as discussed above. In alternative embodiments, the computing system 224 may use the distraction force measurement to determine the distraction distance measurement (e.g., gap measurement) based on algorithms, system preferences, anatomical data, virtual bone models, etc. In some embodiments, the graphical user interface 508 may also display the distraction force measurement (e.g., as a cross-hatch, ex, bubble, dot, column, bars, stacks, etc.), the gap measurement (e.g., as a bar, in numerical form, etc.), and/or a visualization of the live tracked distraction device. In some embodiments, the distraction force measurement may be at a specific contact point (e.g., the distraction force at an anatomical structure, the medial condyle, the lateral condyle, etc.) and the gap measurement may be placed near the virtual bone model relative to the measurements, in a table, or in any other way suitable to display information (see FIGS. 13-16).

At step 1204, a determination is made as to whether the distraction force is less than a threshold distraction force. For example, the computing system 224 may be configured to determine a threshold distraction force measurement. The threshold distraction force may be predetermined (e.g., as a result of system requirements, FDA requirements, or other regulatory requirements), set by user-selectable surgeon preferences, or calculated dynamically based on other measurements and anatomical data (e.g., data collected during the initial assessment workflow step 406 of FIG. 4), and may represent the maximum distraction force for which accurate or useful gap measurements can be obtained. In some embodiments, the threshold distraction force measurement may also be displayed on the graphical user interface 508. Then, in step 1204, the computing system 224 may determine whether the distraction force measurement obtained in step 1202 is less than the threshold distraction force measurement.

If the computing system 224 determines that the distraction force measurement obtained in step 1202 is less than the threshold distraction force measurement, the computing system 224 may proceed to step 1206 and allow capture of gap data (e.g., the lateral gap, the medial gap, both gaps, delta gaps, etc.) to be stored in computing system 224. As discussed in reference to FIG. 6, the gap data may be automatically captured by surgical system 500 (e.g., computing system 224), captured in response to some user input (e.g., pressing a foot pedal, pressing a button in the surgical system 500, pressing a button on graphical user interface 508, via voice command, etc.), or captured in some other means. In some embodiments, the graphical user interface 508 may display the virtual bone model, and compare the distraction force measurement with the threshold distraction force measurement in real-time.

Also at step 1204, if the computing system 224 determines that the distraction force measurement is not less than (e.g., more than) the threshold distraction force measurement, the computing system 224 may proceed to step 1208 and prevent capturing the gap data. In some embodiments, the distraction device may be modified (e.g., moved to change the location of the distraction force) so as to reduce the distraction force on the femur 206 and/or tibia 208, and the process 1200 may be repeated.

The process 1200 of FIG. 12 may be completed using a single, or a plurality of, distraction devices, force sensors, and/or measurement devices. The process 1200 of FIG. 12 may also be repeated for all gap measurements (e.g., medial gap and lateral gap, while the joint is extended or flexed, delta gaps, etc.), or in any combination thereof, in order to obtain the desired gap measurements, force measurements, distance measurements for a surgical procedure, and any other suitable type of measurement (e.g., leg pose measurement, force contact point measurement, and/or joint angle measurements).

Figure 13:
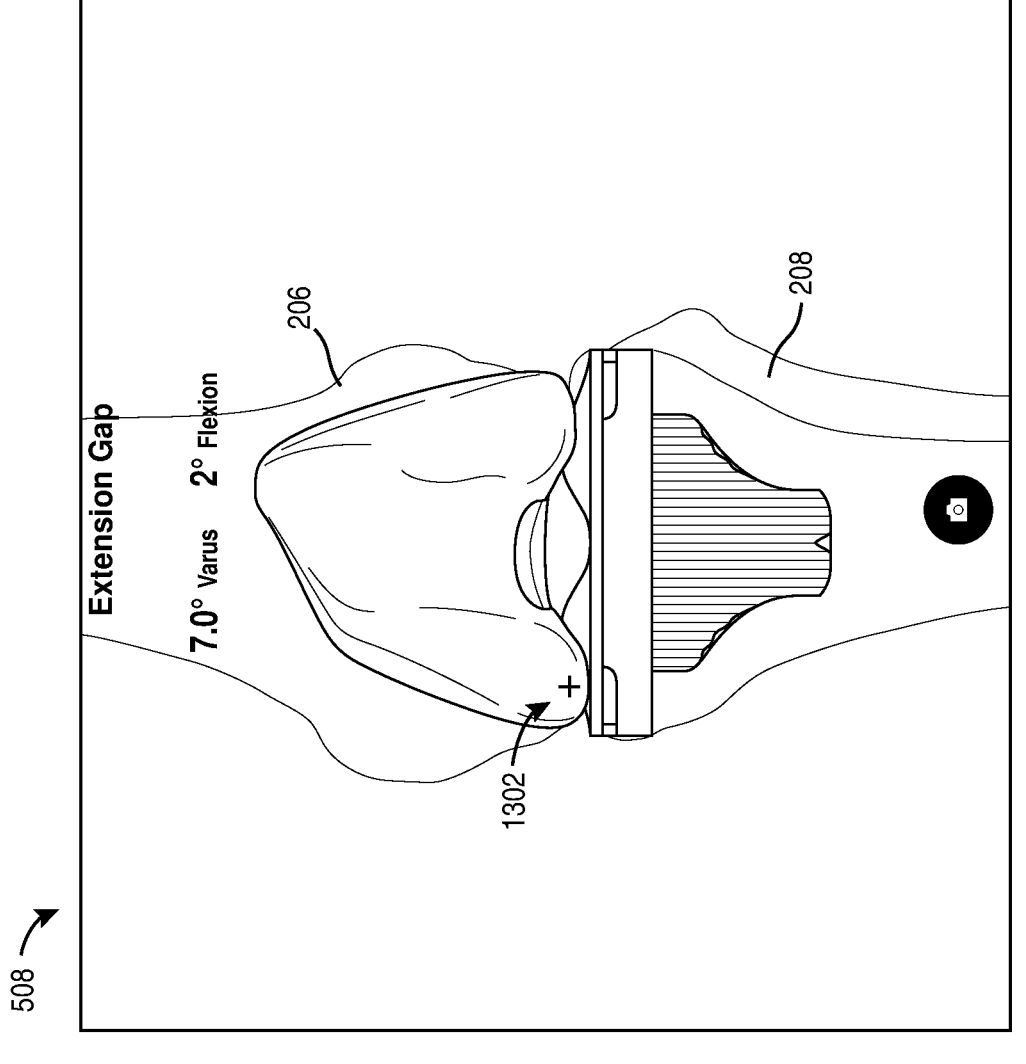
FIG. 13 is an illustration depicting an example implementation of the processes of FIG. 12, according to an exemplary embodiment.

Referring now to FIG. 13, an illustration of a possible graphical interface displayed during implementation of the process of FIG. 12 is shown, according to an exemplary embodiment. The illustration in FIG. 13 may be executed during the process 1200 of FIG. 12, using the surgical system 200 (e.g., or surgical system 500), for example. FIG. 13 illustrates a coronal view of a virtual bone model in a graphical user interface (e.g., graphical user interface 508), which includes a virtual bone model of the femur 206 and the tibia 208, and a distraction force measurement 1302. As discussed above, a distraction device may be used to measure a distraction force measurement 1302 at various locations at the femur 206 and/or the tibia 208 (e.g., the medial gap or the lateral gap, during extension or flexion). The distraction device may provide the surgical system 200 (e.g., the computing system 224) with the distraction force measurement 1302, and the graphical user interface 508 may display the distraction force measurement 1302 on the virtual bone model (e.g., in the form of a cross, hatch, x, number, etc.). As discussed above, in some embodiments the distraction force measurement 1302 may be displayed at a specific point (e.g., the distraction force at an anatomical structure, the medial condyle, the lateral condyle, etc.), and/or if the distraction device is modified (e.g., moved) a distraction force point path may be tracked on the virtual bone model. In some embodiments, the process 1200 of FIG. 12 may be repeated, and additional distraction force measurements may be provided to the surgical system 200, and displayed on the graphical user interface 508 on the virtual bone model (e.g., similar to distraction force measurement 1302).

Figure 14:
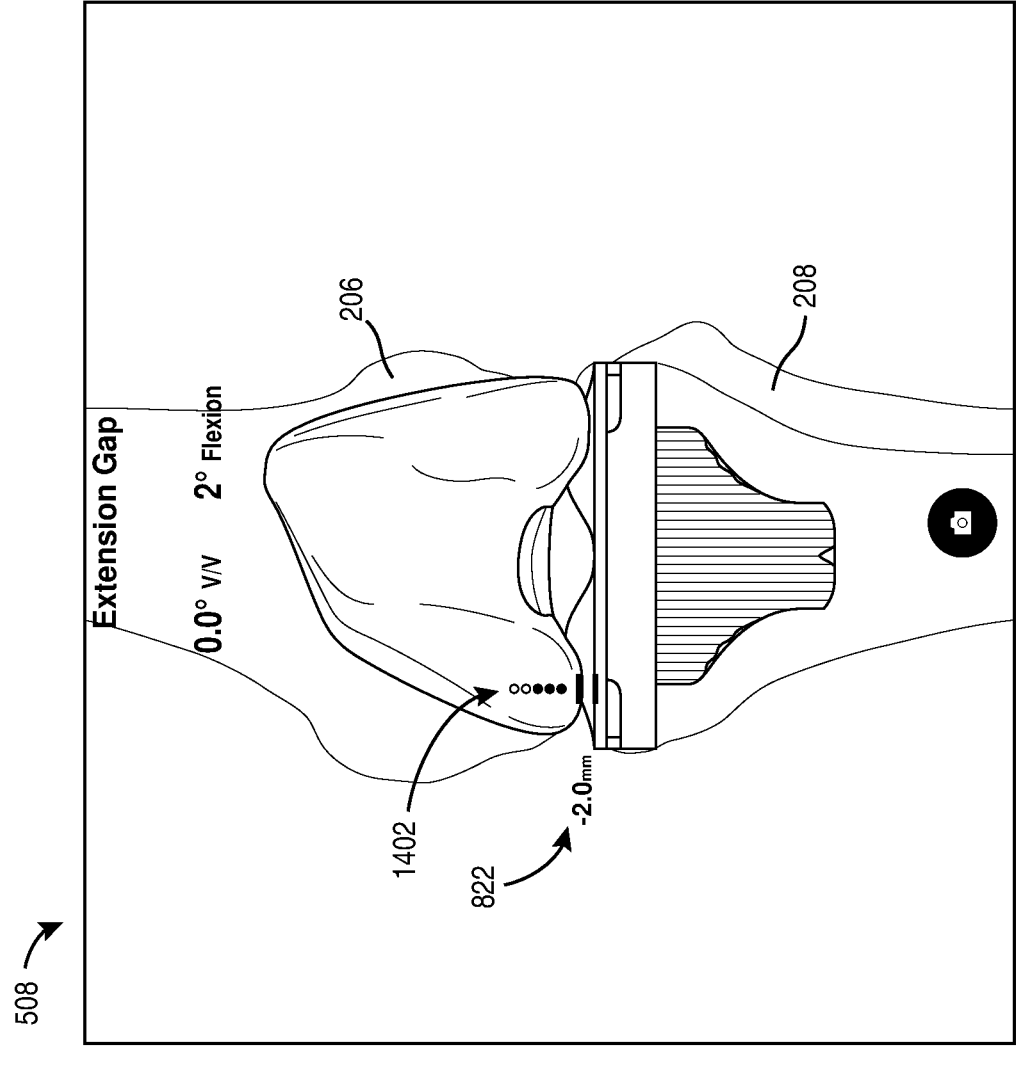
FIG. 14 is another illustration depicting an example implementation of the processes of FIG. 12, according to an exemplary embodiment.

Referring now to FIG. 14, an illustration of another possible graphical interface displayed during implementation of the process of FIG. 12 is shown, according to an exemplary embodiment. The implementation shown in FIG. 14 may be executed during the process 1200 of FIG. 12, using the surgical system 200 (e.g., or surgical system 500), for example. FIG. 14 illustrates a coronal view of a virtual bone model in a graphical user interface (e.g., graphical user interface 508), which includes a virtual bone model of the femur 206 and the tibia 208, a distraction force measurement 1402, and a medial gap measurement 822. As discussed above, a distraction device may be used to measure a distraction force measurement 1402 at various locations at the femur 206 and/or the tibia 208 (e.g., near the medial gap or the lateral gap, during extension or flexion, during a range of motion of a joint, etc.). The distraction device may provide the surgical system 200 (e.g., computing system 224) with the distraction force measurement 1402, and graphical user interface 508 may display the distraction force measurement 1402 (e.g., at a specific contact point or along a path) on the virtual bone model. As shown in FIG. 14, the distraction force measurement 1402 may be displayed in the form of proportionate bubbles; however, it may also be displayed in any other suitable means (e.g., bars, columns, stacks, etc.). In some embodiments, the surgical system 200 (e.g., the computing system 224) may use the distraction force measurement 1402 to determine the medial gap measurement 822 (and/or lateral gap measurement) based on algorithms, system preferences, anatomical data, virtual bone models, etc. In other embodiments, the distraction device may also provide the surgical system 200 (e.g., computing system 224) with the medial gap measurement 822 (and/or lateral gap measurement). The medial gap measurement 822 (and/or lateral gap measurement) may be displayed via the graphical user interface 508 in any suitable form (e.g., in a table, as numerical figures, as bars or columns, on the virtual bone model, etc.).

Figure 15:
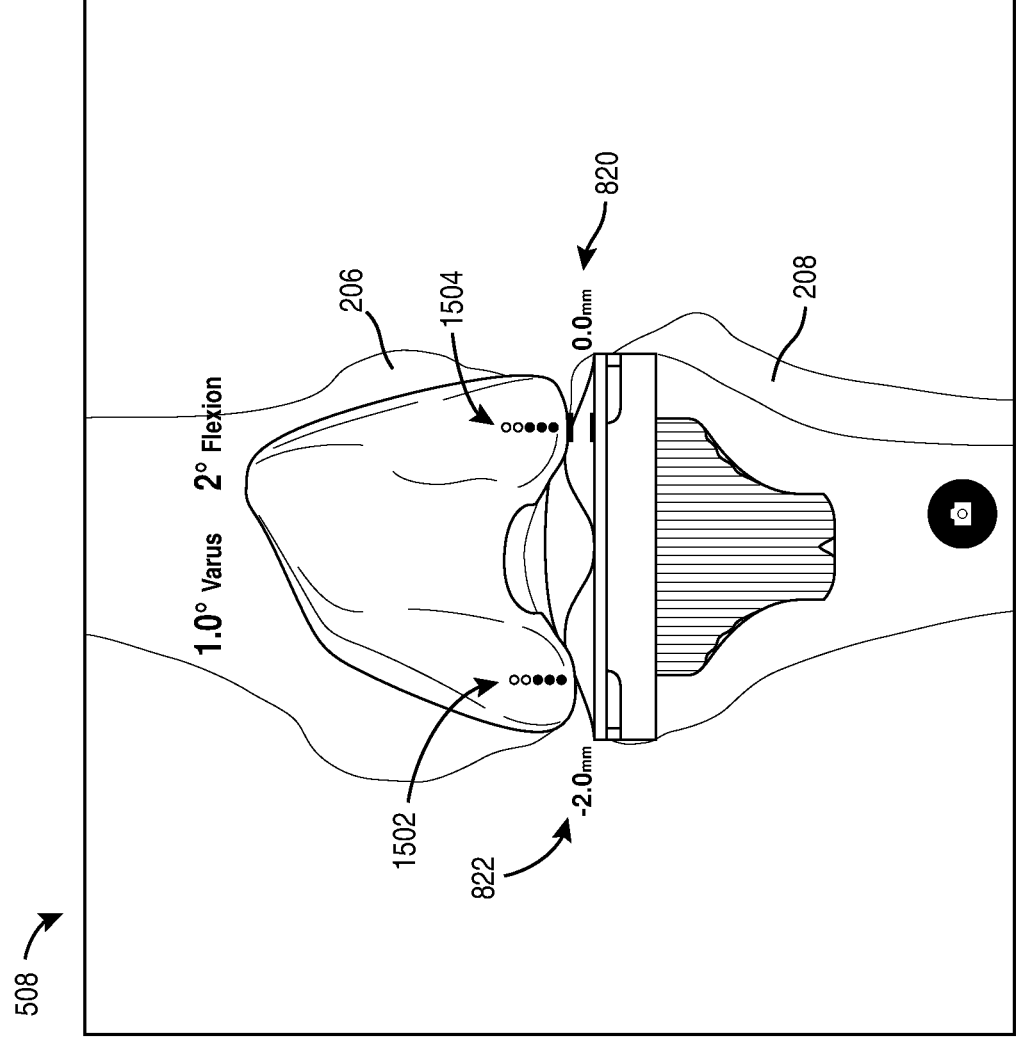
FIG. 15 is yet another illustration depicting an example implementation of the processes of FIG. 12, according to an exemplary embodiment.

Referring now to FIG. 15, an illustration of yet another possible graphical interface displayed during implementation of the process of FIG. 12 is shown, according to an exemplary embodiment. The implementation shown in FIG. 15 may be executed during the process 1200 of FIG. 12, using the surgical system 200 (e.g., or surgical system 500), for example. FIG. 15 illustrates a coronal view of a virtual bone model in graphical user interface 508, which includes a virtual bone model of the femur 206 and the tibia 208, a first distraction force measurement 1502 and a medial gap measurement 822, and a second distraction force measurement 1504 and a lateral gap measurement 820. As discussed above with regard to FIG. 14, a distraction device may be used to measure a first distraction force measurement 1502, at a location at the femur 206 and/or the tibia 208. The graphical user interface 508 may display the first distraction force measurement 1502 (and the medial gap measurement 822) on the virtual bone model. As discussed above, the process 1200 may be repeated, and additional force and gap measurements may be collected. For example, a distraction device may be used to measure a second distraction force measurement 1504 (and determine and/or measure a lateral gap measurement 820), at a different location at the femur 206 and/or tibia 208. The graphical user interface 508 may also display the second distraction force measurement 1504 (and lateral gap measurement 820). In some embodiments, the process 1200 may be repeated for different distraction force measurements, and different gap measurements. Once the distraction force and gap measurements are complete, the data can be stored in computing system 224, and displayed via the graphical user interface 508 in any suitable form (e.g., in a table, as numerical figures, as bars or columns, on the virtual bone model, etc.).

Figure 16:
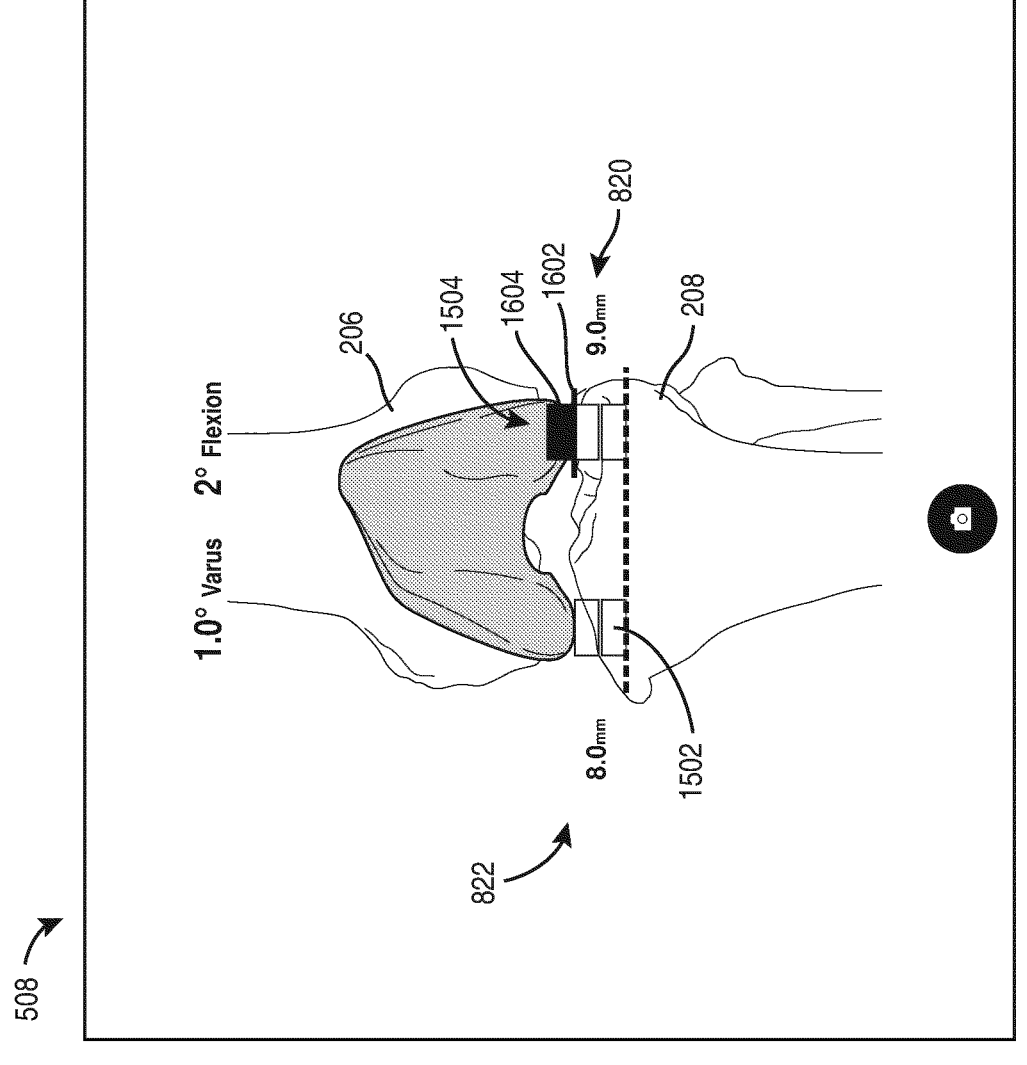
FIG. 16 is yet another illustration depicting an example implementation of the processes of FIG. 12, according to an exemplary embodiment.

Referring now to FIG. 16, an illustration of yet another possible implementation of the process of FIG. 12 is shown, according to an exemplary embodiment. The implementation shown in FIG. 16 may be executed during the process 1200 of FIG. 12, using the surgical system 200 (e.g., surgical system 500), for example. FIG. 16 illustrates a coronal view of a virtual bone model in graphical user interface 508, which includes a virtual bone model of the femur 206 and the tibia 208, a first distraction force measurement 1502 and a medial gap measurement 822, and a second distraction force measurement 1504 and a lateral gap measurement 820. As discussed above, a distraction device may be used to measure a first distraction force measurement 1502, and determine and/or measure medial gap measurement 822, at a location at the femur 206 and/or tibia 208. The illustration in FIG. 16 may show that the first distraction force measurement 1502 was found to be below the threshold distraction force measurement (e.g., in steps 1202-1206 of FIG. 12). As such, the computing system 224 may determine (and/or obtain) the medial gap measurement 822, and the graphical user interface 508 may display the first distraction force measurement 1502 and the medial gap measurement 822 on the virtual bone model.

Also shown in FIG. 16, a distraction device may be used to measure a second distraction force measurement 1504, and determine and/or measure a lateral gap measurement 820, at another location at the femur 206 and/or tibia 208. The illustration in FIG. 16 may show that the second distraction force measurement 1504 was found to be above the threshold distraction force measurement (e.g., in steps 1202-1204, then to 1208 of FIG. 12). This determination (e.g., computing system 224 determining the distraction force was above the threshold) may be displayed via the graphical user interface 508 on the virtual bone model as maximum distraction force measurement 1602, and above threshold distraction force measurement 1604. The maximum distraction force measurement 1602 may depict what computing system 224 determines to be the threshold distraction force measurement in process 1200 (e.g., in step 1204 of FIG. 4). The above threshold distraction force measurement 1604 may depict what computing system 224 determines to be above the threshold distraction force measurement in process 1200. The lateral gap measurement 820 may be displayed via the graphical user interface 508 on the virtual bone model, but may not be determined and/or collected until the second distraction force measurement 1504 is below the threshold force measurement (e.g., the distraction force is modified, moved, decreased, etc.).

In some embodiments of FIG. 16, the distraction force measurements and gap measurements (e.g., medial gap or lateral gap, when the joint is extended, flexed, mid-flexion, and/or any pose between flexion and extension) may be taken relative to a variety of anatomical structures at the femur 206 and/or the tibia 208. For example, the distraction force measurements may be taken at the bone, at a cut (e.g., after a bone resection), at an implant, at a ligament (e.g., an insertion point), or any combination thereof. Similarly, the gap measurements, for example, may be taken from bone-to-bone, cut-to-cut (e.g., after one or more resections), implant-to-implant, or any combination thereof. Furthermore, additional distraction force measurements, gap measurements, and/or other measurements (e.g., ligament laxity, etc.) may be taken at along the length of a ligament (e.g., the medial collateral ligament, posterior cruciate ligament, lateral collateral ligament, anterior cruciate ligament, etc.), which may be used alone or in combination with the other data collected. The tracking system 222, computing system 224, and graphical user interface 508 may all coordinate to provide a virtual bone model on the graphical user interface 508 that illustrate the femur 206 and the tibia 208, with corresponding force measurements, gap measurements, and/or other measurements. The virtual force measurements and/or gap measurements may be modified by computing system 224 to correspond to the combination of bone, cut, and implant measurements that are taken.

Figure 17:
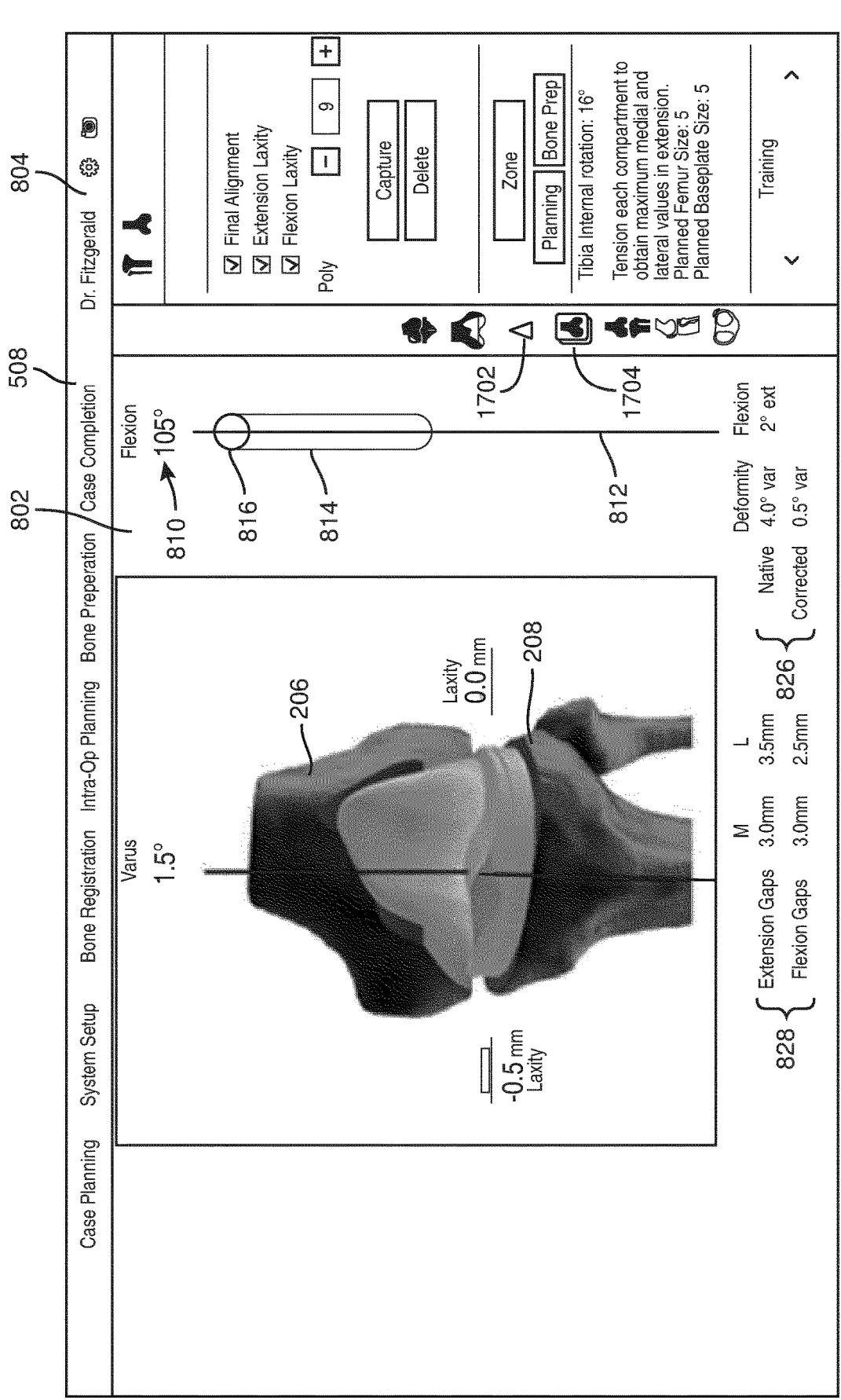
FIG. 17 is another illustration depicting an example implementation of the processes of FIG. 6 and FIG. 7, according to an exemplary embodiment.

Referring now to FIG. 17, an illustration of a possible implementation of the processes of FIG. 6 and FIG. 7 is shown, according to an exemplary embodiment. The illustration shows a coronal view of a virtual bone model in the graphical user interface 508, which may be provided via the display 264 of the surgical system 200 (e.g., surgical system 500) during the initial assessment workflow step 406 of FIG. 4, and/or the mid-resection tensioning workflow or trailing workflow step 412 of FIG. 4. In some embodiments, the illustration of FIG. 17 may be provided during the mid-resection tensioning workflow, or the trialing workflow, of step 412 of FIG. 4 (e.g., following a bone preparation workflow step 410 where one or more cuts, or other bone modifications may be executed), which may provide additional intraoperative information and/or measurements relating to the relative positions of the bones or joint to facilitate soft tissue balancing and/or adjustments to a surgical plan. The graphical user interface 508 may be updated in real-time, to display a real-time virtual bone model of the femur 206 and the tibia 208, or other information and measurements of processes 600 and 700 of FIG. 7. The graphical user interface 508 may also display the information from processes 600 and 700 in model window 802, and/or tab bar 804.

Like FIGS. 8-10, the model window 802 of FIG. 17 displays pose and orientation information relating to the femur 206 and the tibia 208, obtained from the tracking system 222 and/or the computing system 224 (e.g., steps 604-606 of FIG. 6, etc.), for example the flexion angle 810. Similarly, the tracking system 222 and the computing system 224 may determine and display the range of acceptable flexion angles (e.g., via the pill box 814), and the current flexion angle (e.g., via the indicator 816), as discussed above. The tracking system 222 and the computing system 224 may update the graphical user interface 508 in real-time, such that the model window 802 may display the certain measurements in real-time. As discussed above with regard to FIGS. 6-7, as the joint is manipulated the measurements may change in real-time (e.g., "ratchet" upwards, downwards, etc.).

As mentioned above with regard to FIG. 6, and as shown in FIG. 17, the model window 802 and/or the tab bar 804 may include a delta gap icon 1702. In an exemplary embodiment, the delta gap icon 1702 may be available during certain stages of a surgical plan (e.g., the mid-resection tensioning workflow, or the trialing workflow, of step 412 of FIG. 4). When the delta gap icon 1702 is available, a user may collect and/or capture a delta measurement (e.g., minimum laxity value) when the joint is within predetermined extension/flexion ranges (e.g., −90 degrees to 45 degrees, including −20 degrees, 0 degrees, 45 degrees; 45 degrees to 270 degrees, including 65 degrees, 85 degrees, 105 degrees, etc.). The delta measurement may be used as a zero-value measurement (e.g., a baseline measurement) relative to certain measurements, discussed above (e.g., real-time gap measurements, maximum gap measurements, flexion angle measurements, etc.). As such, when the delta gap icon 1702 is selected, the gap measurement may be set as the zero-value measurement, and all subsequent measurements (e.g., real-time gap, maximum, angle, etc.) may be measured (calculated, scaled, defined, etc.) relative to the delta measurement. This feature enables gap measurements and gap-data-related-displays to be referenced relative to a real/actual minimum gap (e.g., at which trial implants are touching), so that the values correspond to a user's intuitive understanding of joint laxity and the actual distance between the two implants.

In an exemplary embodiment, the delta gap icon 1702 may be enabled or disabled via an input from the user (e.g., press a button, a foot pedal, voice command, etc.). In some embodiments, the delta gap icon 1702 may be enabled in order to provide a delta measurement relative to a point at a bone (e.g., an anatomical structure, the medial condyle, the lateral condyle, etc.), a point at a cut (e.g., after a bone resection), a point at an implant (e.g., a femoral implant, a tibial implant, etc.), or at any other suitable anatomical structure or component. In an exemplary embodiment, after the delta gap icon 1702 is selected (e.g., the delta gap measurement is collected and captured), the measurements in the angle measurement table 826 and the gap measurement table 828 may be updated relative to the delta gap measurement. In this regard, the delta gap icon 1702 (and the delta gap measurement) may be used to zero out any errors (i.e., deviations from a pre-operative plan) incurred during implementation of the surgical plan.

Further, after the delta gap icon 1702 is selected, real-time measurements may be determined relative to the delta gap measurement, and the model window 802 may display the relative measurements (e.g., relative to the delta gap measurement) in real-time. In an exemplary embodiment, the delta gap measurement may be collected and/or captured through processes similar to those described in FIGS. 6-7. For example, the delta gap measurement may be collected similar to process 600 described above in FIG. 6 (e.g., the delta gap measurement may be collected and/or captured when the current flexion angle is within the range of predetermined flexion angles). Similarly, the delta gap measurement may be collected similar to process 700 described above in FIG. 7 (e.g., the delta gap measurement may be collected and/or captured through an iterative process, and a maximum delta gap measurement may be captured).

Also as mentioned above with regard to FIGS. 7-8, and as shown in FIG. 17, the model window 802 and/or the tab bar 804 may include a pose review icon 1704. In an exemplary embodiment, the pose review icon 1704 may become enabled after a first angle measurement is populated in the angle measurement table 826 and/or a first gap measurement is populated in the gap measurement table 828. In some embodiments, the pose review icon 1704 may be enabled and/or disabled. When the pose review icon 1704 is enabled, a user may review an angle measurement and/or a gap measurement by selecting the measurement from the tables 826 and/or 828, which provides (e.g., populates) a second model window 802 that contains the information captured during the selected measurement. For example, when a user selects a first gap measurement from the gap measurement table 828, the second model window 802 may be populated with the information captured during the first gap measurement (e.g., the virtual bone model of the femur 206 and the tibia 208, the angle measurement table 826, the flexion angle, e.g., indicator 816, the acceptable range of flexion angles, e.g., the pill box 814, the maximum gap values, etc.). In an exemplary embodiment, the second model window 802 may be populated with information that is a displayed differently (e.g., a different color, font, location, etc.). In some embodiments, after the user selects the pose review icon 1704, the user may modify the data populated in the second model window 802. In other embodiments, after the user selects the pose review icon 1704, the user may only view the data populated in the second model window 802.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (e.g., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of various systems (e.g., system 100, system 200, etc.) and methods as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A surgical system comprising:
a tracking system configured to obtain data indicative of a pose of a first bone of a joint and a pose of a second bone of the joint;
a display device configured to display a graphical user interface;
circuitry configured to:
determine a range of flexion angles of the joint for a gap capture step for assessing a gap distance between the first bone and the second bone, wherein the range of flexion angles is a portion of a full range of motion of the joint;
determine, in real-time, a current flexion angle of the joint based on the data from the tracking system;

control the display device to provide, via the graphical user interface and in real-time, a visualization of the current flexion angle relative to the range of flexion angles for the gap capture step; and
provide the gap capture step in real-time by:
in response to determining the current flexion angle is inside the range of flexion angles for the gap capture step, capturing the gap distance between the first bone and the second bone based on the data from the tracking system;
in response to determining the current flexion angle is outside the range of flexion angles for the gap capture step, preventing the capture of the gap distance.

2. The surgical system of claim 1, wherein the range of flexion angles is based on an offset from a measured flexion angle of the joint when the joint is at a maximum extension.

3. The surgical system of claim 1, wherein in response to determining the current flexion angle is inside the range of flexion angles for the gap capture step, providing the gap capture step includes:
capturing a first gap measurement by determining, based on the data from the tracking system, a first gap between the first bone and the second bone achieved at a first time.

4. The surgical system of claim 3, wherein in response to determining the current flexion angle is inside the range of flexion angles for the gap capture step, providing the gap capture step includes:
capturing a second gap measurement by determining, based on the data from the tracking system, a second gap between the first bone and the second bone achieved at a second time.

5. The surgical system of claim 4, wherein the circuitry is further configured to:
determine whether the second gap measurement is larger than the first gap measurement; and
in response to determining the second gap measurement is larger than the first gap measurement, set the second gap measurement as a maximum gap measurement.

6. The surgical system of claim 1, wherein the surgical system further comprises a distraction device comprising a force sensor, wherein the distraction device is configured to distract the joint and collect distraction force data at the joint to determine a distraction force.

7. The surgical system of claim 6, wherein the circuitry is further configured to:
obtain a threshold distraction force;
receive the distraction force data from the distraction device; and
in response to receiving the distraction force data, determine whether the distraction force is less than the threshold distraction force.

8. The surgical system of claim 7, wherein the circuitry is further configured to:
determine whether the distraction force is less than the threshold distraction force; and
in response to determining the distraction force data is less than the threshold distraction force, providing the gap capture step includes capturing a first gap measurement by determining, based on the data from the tracking system, a first gap between the first bone and the second bone achieved during the duration of a first gap capture step.

9. A method of controlling a surgical system, comprising:
obtaining a surgical plan comprising a plurality of planned measurements;

obtaining tracking data indicative of a pose of a first bone of a joint and a pose of a second bone of the joint from a tracking system;

determining a range of flexion angles of the joint for a gap capture step for assessing a gap distance between the first bone and the second bone, wherein the range of flexion angles is a portion of a full range of motion of the joint;

determining, in real-time, a current flexion angle of the joint based on the tracking data from the tracking system;

instructing a display to display, via a graphical user interface and in real-time, a visualization of the current flexion angle relative to the range of flexion angles for the gap capture step; and providing the gap capture step in real-time by: in response to determining the current flexion angle is inside the range of flexion angles for the gap capture step, capturing the gap distance between the first bone and the second bone based on the data from the tracking system;

in response to determining the current flexion angle is outside the range of flexion angles for the gap capture step, preventing the capture of the gap distance.

10. The method of claim 9, wherein the range of flexion angles is based on an offset from a measured flexion angle of the joint when the joint is at a maximum extension.

11. The method of claim 9, wherein in response to determining the current flexion angle is inside the range of flexion angles for the gap capture step, providing the gap capture step includes:

capturing a first gap measurement by determining, based on the tracking data from the tracking system, a first gap between the first bone and the second bone achieved at a first time.

12. The method of claim 11, wherein in response to determining the current flexion angle is inside the range of flexion angles for the gap capture step, providing the gap capture step includes:

capturing a second gap measurement by determining, based on the tracking data from the tracking system, a second gap between the first bone and the second bone achieved at a second time.

13. The method of claim 12, further comprising:

in response to determining the second gap measurement is larger than the first gap measurement, set the second gap measurement as a maximum gap measurement.

14. The method of claim 9, further comprising:

receiving distraction force data at the joint from a distraction device, which is configured to distract the first bone and the second bone, and comprises a plurality of force sensors; and determining a threshold distraction force at the joint.

15. The method of claim 14, further comprising:

determining whether the distraction force is less than the threshold distraction force; and in response to determining the distraction force is more than the threshold distraction force, preventing the gap capture step.

16. The method of claim 14, further comprising:

determining whether the distraction force is less than the threshold distraction force; and preventing the capturing of the gap distance between the first bone and the second bone in response to determining the distraction force not being less than the threshold distraction force.

17. One or more non-transitory computer-readable media storing program instructions that, when executed by one or more processors, causes the one or more processors to perform operations comprising:

obtaining a surgical plan comprising a plurality of planned measurements;

obtaining tracking data indicative of a pose of a first bone of a joint and a pose of a second bone of the joint from a tracking system;

determining a range of flexion angles of the joint for a gap capture step for assessing a gap distance between the first bone and the second bone, wherein the range of flexion angles is a portion of a full range of motion of the joint;

determining, in real-time, a current flexion angle of the joint based on the tracking data from the tracking system;

providing a graphical user interface in real-time, which comprises providing a visualization of the current flexion angle relative to the range of flexion angles for the gap capture step; and providing the gap capture step in real-time by:

in response to determining the current flexion angle is inside the range of flexion angles for the gap capture step, capturing the gap distance between the first bone and the second bone based on the data from the tracking system;

in response to determining the current flexion angle is outside the range of flexion angles for the gap capture step, preventing the capture of the gap distance.

18. The non-transitory computer-readable media of claim 17, wherein the range of flexion angles is based on an offset from a measured flexion angle of the joint when the joint is at a maximum extension.

19. The non-transitory computer-readable media of claim 17, wherein in response to determining the current flexion angle is inside the range of flexion angles for the gap capture step, providing the gap capture step includes:

capturing a first gap measurement by determining, based on the tracking data from the tracking system, a first gap between the first bone and the second bone achieved at a first time.

20. The non-transitory computer-readable media of claim 19, wherein in response to determining the current flexion angle is inside the range of flexion angles for the gap capture step, providing the gap capture step includes:

capturing a second gap measurement by determining, based on the tracking data from the tracking system, a second gap between the first bone and the second bone achieved at a second time.

* * * * *